(12) United States Patent
Parys et al.

(10) Patent No.: US 10,987,131 B2
(45) Date of Patent: Apr. 27, 2021

(54) TISSUE CONTAINMENT SYSTEMS AND RELATED METHODS

(71) Applicant: CooperSurgical, Inc., Trumbull, CT (US)

(72) Inventors: James R. Parys, Wallingford, CT (US); Rodrigo DaSilva, Waterbury, CT (US)

(73) Assignee: CooperSurgical, Inc., Trumbull, CT (US)

( * ) Notice: Subject to any disclaimer, the term of this patent is extended or adjusted under 35 U.S.C. 154(b) by 210 days.

(21) Appl. No.: 15/937,911

(22) Filed: Mar. 28, 2018

(65) Prior Publication Data
US 2018/0338773 A1 Nov. 29, 2018

Related U.S. Application Data

(60) Provisional application No. 62/511,007, filed on May 25, 2017.

(51) Int. Cl.
A61B 17/32 (2006.01)
A61B 1/313 (2006.01)
A61B 17/00 (2006.01)
A61B 17/34 (2006.01)
A61M 13/00 (2006.01)
A61B 1/12 (2006.01)

(52) U.S. Cl.
CPC ........ *A61B 17/3423* (2013.01); *A61B 1/3132* (2013.01); *A61B 17/32002* (2013.01); *A61B 1/127* (2013.01); *A61B 17/3474* (2013.01); *A61B 2017/00287* (2013.01); *A61B 2017/00477* (2013.01); *A61B 2017/320024* (2013.01); *A61B 2017/320064* (2013.01); *A61B 2017/3466* (2013.01); *A61M 13/003* (2013.01); *A61M 2202/0225* (2013.01)

(58) Field of Classification Search
CPC ........ A61B 2017/00287; A61B 1/3132; A61B 17/3423; A61B 17/32002
See application file for complete search history.

(56) References Cited

U.S. PATENT DOCUMENTS

| | | | |
|---|---|---|---|
| 5,037,379 | A | 8/1991 | Clayman et al. |
| 5,143,082 | A | 9/1992 | Kindberg et al. |
| 5,279,539 | A | 1/1994 | Bohan et al. |
| 5,330,483 | A | 7/1994 | Heaven et al. |
| 5,336,237 | A | 8/1994 | Chin et al. |
| 5,337,754 | A | 8/1994 | Heaven et al. |
| 5,341,815 | A | 8/1994 | Cofone et al. |

(Continued)

*Primary Examiner* — Sarah W Aleman
(74) *Attorney, Agent, or Firm* — Fish & Richardson P.C.

(57) ABSTRACT

A tissue containment system includes a bag body, a member extending from the bag body and defining a channel, and a viewing window. The bag body at least partially defines an interior region configured to contain a loose tissue specimen and defines an opening sized to receive the loose tissue specimen. The bag body is configured such that a first portion of the bag body can be disposed in an abdominal cavity of a patient while a second portion of the bag body extends outside of the patient. The viewing window is at least partially transparent and provides a seal between the interior region of the bag body and an ambient environment. The channel of the member is configured to receive a tissue visualization device that can be used to view the interior region of the containment bag through the viewing window.

17 Claims, 17 Drawing Sheets

(56) References Cited

U.S. PATENT DOCUMENTS

| | | |
|---|---|---|
| 5,439,474 A | 8/1995 | Li |
| 5,443,472 A | 8/1995 | Li |
| 5,520,634 A | 5/1996 | Fox et al. |
| 5,524,633 A | 6/1996 | Heaven et al. |
| 5,562,694 A | 10/1996 | Sauer et al. |
| 5,569,284 A | 10/1996 | Young et al. |
| 5,575,293 A | 11/1996 | Miller et al. |
| 5,611,803 A | 3/1997 | Heaven et al. |
| 5,618,296 A * | 4/1997 | Sorensen ......... A61B 17/32002 606/167 |
| 5,643,304 A | 7/1997 | Schechter et al. |
| 5,647,372 A | 7/1997 | Tovey et al. |
| 5,685,840 A | 11/1997 | Schechter et al. |
| 5,730,752 A | 3/1998 | Alden et al. |
| 5,735,289 A | 4/1998 | Pfeffer et al. |
| 5,769,794 A | 6/1998 | Conlan et al. |
| 5,827,217 A | 10/1998 | Silver et al. |
| 5,840,077 A | 11/1998 | Rowden et al. |
| 5,980,544 A | 11/1999 | Vaitekunas |
| 6,024,751 A | 2/2000 | Lovato et al. |
| 6,032,673 A | 3/2000 | Savage et al. |
| 6,039,748 A | 3/2000 | Savage et al. |
| 6,045,566 A | 4/2000 | Pagedas |
| 6,113,594 A | 9/2000 | Savage |
| 6,152,932 A | 11/2000 | Ternstrom |
| 6,156,049 A | 12/2000 | Lovato et al. |
| 6,159,160 A | 12/2000 | Hsei et al. |
| 6,162,235 A | 12/2000 | Vaitekunas |
| 6,193,715 B1 | 2/2001 | Wrublewski et al. |
| 6,344,026 B1 | 2/2002 | Burbank et al. |
| 6,350,267 B1 | 2/2002 | Stefanchik |
| 6,406,440 B1 | 6/2002 | Stefanchik |
| 6,419,639 B2 | 7/2002 | Walther et al. |
| 6,468,228 B1 | 10/2002 | Topel et al. |
| 6,506,176 B1 | 1/2003 | Mittelstein et al. |
| 6,537,273 B1 | 3/2003 | Sosiak et al. |
| 6,565,561 B1 | 5/2003 | Goble et al. |
| 6,590,167 B2 | 7/2003 | Clare |
| 6,602,265 B2 | 8/2003 | Dubrul et al. |
| 6,659,105 B2 | 12/2003 | Burbank et al. |
| 6,676,658 B2 | 1/2004 | Burbank et al. |
| 6,997,926 B2 | 2/2006 | Gellman et al. |
| 7,232,439 B2 | 6/2007 | Ciarrocca |
| 7,278,994 B2 | 10/2007 | Goble |
| 7,357,801 B2 | 4/2008 | Burbank et al. |
| 7,491,210 B2 | 2/2009 | Dubrul et al. |
| 7,641,651 B2 | 1/2010 | Nezhat et al. |
| 7,670,346 B2 | 3/2010 | Whitfield |
| 7,740,624 B2 | 6/2010 | Klein et al. |
| 7,762,959 B2 | 7/2010 | Bilsbury |
| 7,815,629 B2 | 10/2010 | Klein et al. |
| 7,909,817 B2 | 3/2011 | Griffin et al. |
| 8,025,670 B2 | 9/2011 | Sharp et al. |
| 8,062,214 B2 | 11/2011 | Shener et al. |
| 8,100,928 B2 | 1/2012 | Nohilly et al. |
| 8,109,961 B2 | 2/2012 | Deshmukh |
| 8,152,820 B2 | 4/2012 | Mohamed et al. |
| 8,162,966 B2 | 4/2012 | Connor et al. |
| 8,167,941 B2 | 5/2012 | Boyd et al. |
| 8,226,549 B2 | 7/2012 | Kumar et al. |
| 8,286,899 B2 | 10/2012 | Schowalter et al. |
| 8,343,148 B2 | 1/2013 | Fleming et al. |
| 8,349,255 B2 | 1/2013 | Schowalter et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,444,655 B2 | 5/2013 | Parihar et al. |
| 8,464,925 B2 | 6/2013 | Hull et al. |
| 8,468,891 B2 | 6/2013 | Chekan et al. |
| 8,491,497 B2 | 7/2013 | Houser et al. |
| 8,491,526 B2 | 7/2013 | Cronin et al. |
| 8,528,563 B2 | 9/2013 | Gruber |
| 8,529,561 B2 | 9/2013 | Griffin et al. |
| 8,535,239 B2 | 9/2013 | Conlon et al. |
| 8,568,424 B2 | 10/2013 | Shugrue et al. |
| 8,574,146 B2 | 11/2013 | Gillespie, Jr. et al. |
| 8,579,914 B2 | 11/2013 | Menn et al. |
| 8,585,725 B2 | 11/2013 | Duperior et al. |
| 8,636,734 B2 | 1/2014 | Burbank et al. |
| 8,641,641 B2 | 2/2014 | Cronin et al. |
| 8,646,674 B2 | 2/2014 | Schulte et al. |
| 8,647,349 B2 | 2/2014 | Gruber et al. |
| 8,652,147 B2 | 2/2014 | Hart |
| 8,702,644 B2 | 4/2014 | Hall et al. |
| 8,714,360 B2 | 5/2014 | Swayze et al. |
| 8,795,278 B2 | 8/2014 | Schmitz et al. |
| 8,795,291 B2 | 8/2014 | Davis et al. |
| 8,808,319 B2 | 8/2014 | Houser et al. |
| 8,821,377 B2 | 9/2014 | Collins |
| 8,834,487 B2 | 9/2014 | Gruber et al. |
| 8,840,625 B2 | 9/2014 | Adams et al. |
| 8,840,626 B2 | 9/2014 | Adams et al. |
| 8,858,538 B2 | 10/2014 | Belson et al. |
| 8,858,546 B2 | 10/2014 | Hall et al. |
| 8,911,363 B2 | 12/2014 | Kumar et al. |
| 8,920,431 B2 * | 12/2014 | Shibley ............... A61J 1/10 606/114 |
| 8,932,316 B2 | 1/2015 | Keast et al. |
| 8,945,021 B2 | 2/2015 | Chin |
| 8,956,286 B2 | 2/2015 | Shibley et al. |
| 8,974,400 B2 | 3/2015 | Swayze et al. |
| 8,986,321 B2 | 3/2015 | Parihar et al. |
| 8,986,331 B2 | 3/2015 | Chekan et al. |
| 9,017,340 B2 | 4/2015 | Davis |
| 9,028,398 B2 | 5/2015 | Kumar et al. |
| 9,044,210 B1 | 6/2015 | Hoyte et al. |
| 9,055,967 B1 | 6/2015 | Polo |
| 9,055,995 B2 | 6/2015 | Solovay et al. |
| 9,072,431 B2 | 7/2015 | Adams et al. |
| 9,113,848 B2 | 8/2015 | Fleming et al. |
| 9,123,261 B2 | 9/2015 | Lowe |
| 9,138,210 B2 | 9/2015 | Schulte et al. |
| 9,155,453 B2 | 10/2015 | Kumar et al. |
| 9,155,454 B2 | 10/2015 | Sahney et al. |
| 9,168,057 B2 | 10/2015 | Poulsen |
| 9,198,687 B2 | 12/2015 | Fulkerson et al. |
| 9,364,253 B1 | 6/2016 | Polo |
| 9,370,341 B2 | 6/2016 | Ceniccola et al. |
| 9,392,935 B2 | 7/2016 | Adams et al. |
| 9,393,033 B2 | 7/2016 | Zerfas et al. |
| 9,510,809 B2 | 12/2016 | Burbank et al. |
| 9,510,853 B2 | 12/2016 | Aljuri et al. |
| 9,522,034 B2 | 12/2016 | Johnson et al. |
| 9,539,018 B2 | 1/2017 | Sartor et al. |
| 9,566,050 B2 | 2/2017 | Seckin |
| 2001/0051810 A1 | 12/2001 | Dubrul et al. |
| 2003/0125639 A1 | 7/2003 | Fisher et al. |
| 2003/0149442 A1 | 8/2003 | Gellman et al. |
| 2003/0195537 A1 | 10/2003 | Dubrul et al. |
| 2003/0236544 A1 * | 12/2003 | Lunsford ........... A61B 17/3462 606/190 |
| 2004/0102770 A1 | 5/2004 | Goble |
| 2004/0243157 A1 | 12/2004 | Connor et al. |
| 2005/0277900 A1 | 12/2005 | Klein et al. |
| 2006/0047185 A1 | 3/2006 | Shener et al. |
| 2006/0058776 A1 | 3/2006 | Bilsbury |
| 2006/0200169 A1 | 9/2006 | Sniffin |
| 2006/0200170 A1 | 9/2006 | Aranyi |
| 2006/0229639 A1 | 10/2006 | Whitfield |
| 2006/0282068 A1 | 12/2006 | Griffin et al. |
| 2007/0027450 A1 | 2/2007 | Nezhat et al. |
| 2007/0135780 A1 | 6/2007 | Pagedas |
| 2007/0135781 A1 | 6/2007 | Hart |
| 2008/0039884 A1 | 2/2008 | Nohilly et al. |
| 2008/0058846 A1 | 3/2008 | Vosough |
| 2008/0065021 A1 | 3/2008 | Jenkins et al. |
| 2008/0091061 A1 | 4/2008 | Kumar et al. |
| 2008/0091071 A1 | 4/2008 | Kumar et al. |
| 2008/0091074 A1 | 4/2008 | Kumar et al. |
| 2008/0091146 A1 | 4/2008 | Solovay et al. |
| 2008/0097468 A1 | 4/2008 | Adams et al. |
| 2008/0097469 A1 | 4/2008 | Gruber et al. |

(56) References Cited

U.S. PATENT DOCUMENTS

| | | |
|---|---|---|
| 2008/0097470 A1 | 4/2008 | Gruber et al. |
| 2008/0097471 A1 | 4/2008 | Adams et al. |
| 2008/0103412 A1 | 5/2008 | Chin |
| 2008/0119868 A1 | 5/2008 | Sharp et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0281323 A1 | 11/2008 | Burbank et al. |
| 2009/0030437 A1 | 1/2009 | Houser et al. |
| 2009/0143639 A1 | 6/2009 | Stark |
| 2009/0182292 A1 | 7/2009 | Egle et al. |
| 2009/0292281 A1 | 11/2009 | Fleming et al. |
| 2009/0292355 A1 | 11/2009 | Boyd et al. |
| 2009/0306471 A1 | 12/2009 | Gettman |
| 2009/0326546 A1 | 12/2009 | Mohamed et al. |
| 2010/0087798 A1 | 4/2010 | Adams et al. |
| 2010/0106130 A1 | 4/2010 | Solovay et al. |
| 2010/0152746 A1 | 6/2010 | Ceniccola et al. |
| 2010/0217299 A1 | 8/2010 | Williams et al. |
| 2010/0219091 A1 | 9/2010 | Turner |
| 2010/0222802 A1 | 9/2010 | Gillespie et al. |
| 2010/0234687 A1 | 9/2010 | Azarbarzin et al. |
| 2010/0305566 A1 | 12/2010 | Rosenblatt et al. |
| 2011/0054488 A1 | 3/2011 | Gruber et al. |
| 2011/0071359 A1 | 3/2011 | Bonadio et al. |
| 2011/0082442 A1 | 4/2011 | Solovay et al. |
| 2011/0118544 A1 | 5/2011 | Adams et al. |
| 2011/0160740 A1 | 6/2011 | Makower et al. |
| 2011/0184311 A1 | 7/2011 | Parihar et al. |
| 2011/0184430 A1 | 7/2011 | Parihar et al. |
| 2011/0184431 A1 | 7/2011 | Parihar et al. |
| 2011/0184432 A1 | 7/2011 | Parihar et al. |
| 2011/0184433 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190782 A1 | 8/2011 | Fleming et al. |
| 2011/0230872 A1 | 9/2011 | Griffin et al. |
| 2011/0264091 A1 | 10/2011 | Koppleman et al. |
| 2011/0281297 A1 | 11/2011 | Chekan et al. |
| 2011/0281319 A1 | 11/2011 | Swayze et al. |
| 2011/0281350 A1 | 11/2011 | Schowalter et al. |
| 2011/0282238 A1 | 11/2011 | Houser et al. |
| 2011/0282239 A1 | 11/2011 | Conlon et al. |
| 2011/0282241 A1 | 11/2011 | Swayze et al. |
| 2011/0282242 A1 | 11/2011 | Cronin et al. |
| 2011/0282270 A1 | 11/2011 | Hall et al. |
| 2011/0282337 A1 | 11/2011 | Hall et al. |
| 2011/0282354 A1 | 11/2011 | Schulte et al. |
| 2011/0282368 A1 | 11/2011 | Swayze et al. |
| 2011/0282372 A1 | 11/2011 | Schowalter et al. |
| 2011/0282373 A1 | 11/2011 | Chekan et al. |
| 2011/0282381 A1 | 11/2011 | Cronin et al. |
| 2011/0282446 A1 | 11/2011 | Schulte et al. |
| 2012/0010464 A1 | 1/2012 | Adams et al. |
| 2012/0016399 A1 | 1/2012 | Poulsen |
| 2012/0078038 A1 | 3/2012 | Sahney et al. |
| 2012/0109144 A1 | 5/2012 | Chin et al. |
| 2012/0109172 A1 | 5/2012 | Schmitz et al. |
| 2012/0150179 A1 | 6/2012 | Feinberg et al. |
| 2012/0191118 A1 | 7/2012 | Chin |
| 2012/0271110 A1 | 10/2012 | Kumar et al. |
| 2012/0277758 A1 | 11/2012 | Davis et al. |
| 2012/0316572 A1 | 12/2012 | Rosenblatt et al. |
| 2013/0090642 A1 | 4/2013 | Shadduck et al. |
| 2013/0123797 A1 | 5/2013 | Livneh |
| 2013/0131445 A1 | 5/2013 | Zerfas et al. |
| 2013/0131457 A1 | 5/2013 | Seckin |
| 2013/0150832 A1 | 6/2013 | Belson et al. |
| 2013/0184536 A1 | 7/2013 | Shibley et al. |
| 2013/0218186 A1 | 8/2013 | Dubois et al. |
| 2013/0253267 A1 | 9/2013 | Collins |
| 2014/0011172 A1 | 1/2014 | Lowe |
| 2014/0052018 A1 | 2/2014 | Hawkins |
| 2014/0074072 A1 | 3/2014 | Griffin et al. |
| 2014/0135788 A1 | 5/2014 | Collins |
| 2014/0180070 A1 | 6/2014 | Millett et al. |
| 2014/0180163 A1 | 6/2014 | Burbank et al. |
| 2014/0222015 A1 | 8/2014 | Keast et al. |
| 2014/0236110 A1 | 8/2014 | Taylor et al. |
| 2014/0236167 A1 | 8/2014 | Shibley et al. |
| 2014/0236168 A1 | 8/2014 | Shibley et al. |
| 2014/0257112 A1 | 9/2014 | Siegel |
| 2014/0276913 A1 | 9/2014 | Tah et al. |
| 2014/0288486 A1 | 9/2014 | Hart et al. |
| 2014/0295554 A1 | 10/2014 | Kim et al. |
| 2014/0303659 A1 | 10/2014 | Aljuri et al. |
| 2014/0330285 A1 | 11/2014 | Rosenblatt et al. |
| 2015/0018815 A1 | 1/2015 | Sartor et al. |
| 2015/0018837 A1 | 1/2015 | Sartor et al. |
| 2015/0088107 A1 | 3/2015 | Aljuri et al. |
| 2015/0100076 A1 | 4/2015 | Chin |
| 2015/0144514 A1 | 5/2015 | Brennan et al. |
| 2015/0148615 A1 | 5/2015 | Brennan et al. |
| 2015/0190163 A1 | 7/2015 | Ciulla et al. |
| 2015/0201995 A1 | 7/2015 | Dubois et al. |
| 2015/0258258 A1 | 9/2015 | Bonnette et al. |
| 2015/0272561 A1 | 10/2015 | Kondrup et al. |
| 2015/0272620 A1 | 10/2015 | Zisow |
| 2015/0272621 A1 | 10/2015 | Zisow |
| 2015/0289864 A1 | 10/2015 | Holsten et al. |
| 2015/0289928 A1 | 10/2015 | Masansky |
| 2015/0297254 A1 | 10/2015 | Sullivan et al. |
| 2015/0305728 A1 | 10/2015 | Taylor et al. |
| 2015/0305764 A1 | 10/2015 | Hoyte et al. |
| 2015/0305772 A1 | 10/2015 | McCauley |
| 2015/0320409 A1 | 11/2015 | Lehmann et al. |
| 2015/0335342 A1 | 11/2015 | Hart et al. |
| 2015/0335344 A1 | 11/2015 | Aljuri et al. |
| 2015/0351621 A1 | 12/2015 | Hill et al. |
| 2015/0374400 A1 | 12/2015 | Kumar et al. |
| 2016/0022289 A1 | 1/2016 | Wan |
| 2016/0030073 A1 | 2/2016 | Isakov et al. |
| 2016/0045214 A1 | 2/2016 | Sullivan et al. |
| 2016/0095612 A1 | 4/2016 | DeVille |
| 2016/0095613 A1 | 4/2016 | Trondle |
| 2016/0100857 A1 | 4/2016 | Wachli et al. |
| 2016/0113679 A1 | 4/2016 | Thomas et al. |
| 2016/0135798 A1 | 5/2016 | Macleod et al. |
| 2016/0143778 A1 | 5/2016 | Aljuri et al. |
| 2016/0157843 A1 | 6/2016 | Dickson et al. |
| 2016/0183932 A1 | 6/2016 | Shibley et al. |
| 2016/0199050 A1 | 7/2016 | Radl et al. |
| 2016/0199051 A1 | 7/2016 | Shibley et al. |
| 2016/0242752 A1 | 8/2016 | Dickson |
| 2016/0242808 A1 | 8/2016 | Escudero et al. |
| 2016/0262794 A1 | 9/2016 | Wachli et al. |
| 2016/0296244 A1 | 10/2016 | Thomas et al. |
| 2016/0296284 A1 | 10/2016 | Zerfas et al. |
| 2016/0302783 A1 | 10/2016 | Greenberg et al. |
| 2016/0338682 A1 | 11/2016 | Hoyte et al. |
| 2016/0346000 A1 | 12/2016 | Abreu |
| 2017/0049427 A1 | 2/2017 | Do et al. |

* cited by examiner

TISSUE CONTAINMENT SYSTEMS AND RELATED METHODS

CROSS REFERENCE TO RELATED APPLICATION

This application claims priority to U.S. Provisional Patent Application No. 62/511,007, filed on May 25, 2017, the entire contents of which is incorporated herein by reference.

TECHNICAL FIELD

This disclosure relates to tissue containment systems, related methods, and more particularly to containing tissue morcellated within a body cavity.

BACKGROUND

Laparoscopic surgery is a type of minimally invasive surgery in which procedures may be performed through small openings (e.g., incisions) in an abdominal wall. In many cases, such procedures involve removal of tissues that are suspected of being pathological. In order to remove a tissue mass that is larger than a size of an incision in the abdominal wall, the tissue mass may be reduced in size (e.g., ground up) by a morcellator that has been introduced into the abdominal cavity and withdrawn (e.g., suctioned) from the abdominal cavity through the morcellator. The morcellation process can undesirably spread (e.g., eject) trace amounts of ground tissue within the abdominal cavity, which can unintentionally upstage a disease state in cases where the tissue mass proves to be malignant or otherwise progressive. Therefore, it can be beneficial to contain and isolate morcellated or otherwise reduced tissue from the abdominal cavity during a tissue reduction process carried out within the abdominal cavity.

SUMMARY

This disclosure relates to tissue containment systems and methods of using the tissue containment systems during surgical procedures (e.g., laparoscopic procedures). Such tissue containment systems include a containment bag that has a single opening, while having multiple access ports that may be used for procedural steps, such as introducing a tissue removal device (e.g., a morcellator) into the containment bag, manipulating tissue within the containment bag, and visualizing tissue within the containment bag.

In one aspect, a tissue containment system includes a containment bag configured to be placed in an abdominal cavity of a patient. The containment bag defines a main portion sized to contain a loose tissue specimen within the abdominal cavity, a first portion providing an opening sized to receive the loose tissue specimen and arranged to extend from the main portion outside of the patient while the main portion is disposed within the abdominal cavity, and a second portion arranged to extend from the main portion outside of the patient while the main portion is disposed within the abdominal cavity, the second portion being configured to receive a tissue visualization device. The tissue containment system further includes a viewing window sealed to the second portion, the viewing window being configured such that the tissue visualization device can view an interior region of the containment bag when the tissue visualization device is disposed in the second portion of the containment bag.

Embodiments may include one or more of the following features.

In some embodiments, the main portion, the first portion, and the second portion are in fluid communication with one another.

In certain embodiments, the main portion and the first portion are in fluid communication with each other and fluidly isolated from the second portion.

In some embodiments, the tissue containment system further includes a retainer attached to an external surface of the second portion.

In certain embodiments, the retainer is adjustable from a first extent that is smaller than a wound within a wall of the abdominal cavity for passage through the wound to a second extent that is larger than the wound for retaining an end of the second portion outside of the patient.

In some embodiments, a wall of the containment bag is configured to thermally isolate the interior region of the containment bag from the abdominal cavity.

In certain embodiments, the second portion is formed as a sleeve sized to surround the tissue visualization device.

In some embodiments, the second portion is invertible to provide a double wall layer around the tissue visualization device.

In certain embodiments, the viewing window is adjustable from a first position outside of the patient to a second position within the abdominal cavity while the main portion of the containment bag is disposed within the abdominal cavity.

In some embodiments, an end of the second portion is positionable outside of the patient while the main portion of the containment bag is disposed within the abdominal cavity.

In certain embodiments, the viewing window is positioned along a wall of the main portion of the containment bag.

In some embodiments, the second portion defines an opening that is positionable outside of the patient while the main portion of the containment bag is disposed within the abdominal cavity.

In certain embodiments, the second portion and the viewing window together isolate the tissue visualization device from the loose tissue specimen and from the abdominal cavity.

In some embodiments, the tissue containment system further includes an access cap configured to close the opening of the first portion, the access cap including an entry port through which a tissue removal device can be passed to access an interior region of the containment bag.

In certain embodiments, the tissue containment system further includes a wound liner that is configured to surround the first portion of the containment bag.

In some embodiments, the access cap is configured to be secured to the wound liner in an airtight manner.

In certain embodiments, the tissue containment system further includes a bag introducer configured to introduce the containment bag into the abdominal cavity.

In some embodiments, the entry port for the tissue removal device provides a passageway for the bag introducer.

In certain embodiments, the tissue removal device is a morcellator.

In some embodiments, the tissue visualization device is an endoscope.

In some embodiments, the containment bag has a general shape of a kidney.

In certain embodiments, the first and second portions project from opposite sides of the main portion of the containment bag.

In some embodiments, the closed end of the second portion is a sealed end.

In certain embodiments, the first portion of the containment bag is an open-ended portion.

In some embodiments, the second portion of the containment bag is a closed-ended portion.

In certain embodiments, the tissue removal device is a tissue reduction device.

In another aspect, a method of containing a loose tissue specimen within an abdominal cavity of a patient includes introducing a containment bag into the abdominal cavity, moving a loose tissue specimen within the abdominal cavity into a main portion of the containment bag through an opening of a first portion of the containment bag, positioning the first portion of the containment bag outside of the patient while the main portion is disposed within the abdominal cavity, positioning a second portion of the containment bag outside of the patient while the main portion is disposed within the abdominal cavity, and inserting a tissue visualization device into the second portion to view an interior region of the containment bag with the tissue visualization device through a viewing window that provides a seal between an ambient environment and the interior region of the containment bag.

Embodiments may include one or more of the following features.

In some embodiments, the method further includes inflating the containment bag.

In certain embodiments, the method further includes thermally isolating the interior region of the containment bag from the abdominal cavity.

In some embodiments, positioning the second portion outside of the patient includes pulling a retainer ring attached to an external surface of the second portion through a wound in wall of the abdominal cavity.

In certain embodiments, the retainer is adjustable from a first extent that is smaller than the wound to a second extent that is larger than the wound.

In some embodiments, the method further includes retaining the second portion outside of the patient.

In certain embodiments, the method further includes inserting the tissue visualization device into a sleeve that forms the second portion.

In some embodiments, the method further includes inverting the sleeve to provide a double wall layer around the tissue visualization device.

In certain embodiments, the method further includes adjusting the viewing window from a first position outside of the patient to a second position within the abdominal cavity while the main portion of the containment bag is disposed within the abdominal cavity.

In some embodiments, the method further includes positioning an end of the second portion outside of the patient while the main portion of the containment bag is disposed within the abdominal cavity.

In certain embodiments, the viewing window is positioned along a wall of the main portion of the containment bag.

In some embodiments, the method further includes positioning an opening of the second portion outside of the patient while the main portion of the containment bag is disposed within the abdominal cavity.

In certain embodiments, the method further includes isolating the tissue visualization device from the loose tissue specimen and from the abdominal cavity.

In some embodiments, the method further includes closing the opening of the first portion with an access cap that includes an entry port for the tissue removal device.

In certain embodiments, the method further includes inserting a wound liner into a wound within a wall of the abdominal cavity and passing the first portion of the containment bag through the wound liner.

In some embodiments, the method further includes securing the access cap to the wound liner in an airtight manner.

In some embodiments, the method further includes passing a bag introducer through the entry port of the access cap.

In certain embodiments, the method further includes introducing the containment bag into the abdominal cavity.

In some embodiments, the method further includes morcellating the tissue contained within the main portion of the containment bag.

In certain embodiments, the method further includes viewing the interior region of the containment bag with an endoscope.

In some embodiments, the surgical procedure is a laparoscopic procedure.

In another aspect, a tissue containment system includes a bag body that at least partially defines an interior region configured to contain a loose tissue specimen and that defines an opening sized to receive the loose tissue specimen, the bag body being configured such that a first portion of the bag body can be disposed in an abdominal cavity of a patient while a second portion of the bag body extends outside of the patient. The tissue containment system further includes a member extending from the bag body and defining a channel and a viewing window that is at least partially transparent and that provides a seal between the interior region of the bag body and an ambient environment, the channel of the member being configured to receive a tissue visualization device that can be used to view the interior region of the containment bag through the viewing window.

In some embodiments, the bag body and the member are in fluid communication with each other.

In certain embodiments, the bag body and the member are fluidly isolated from each other.

In some embodiments, the tissue containment system further includes a retainer attached to an external surface of the member.

In some embodiments, the retainer is adjustable from a first extent that is smaller than a wound within a wall of the abdominal cavity for passage through the wound to a second extent that is larger than the wound for retaining the member outside of the patient.

In certain embodiments, wherein a wall of the bag body is configured to thermally isolate the interior region of the bag body from the abdominal cavity.

In some embodiments, the member is formed as a sleeve sized to surround the tissue visualization device.

In certain embodiments, the member is invertible to provide a double wall layer around the tissue visualization device.

In some embodiments, the viewing window is adjustable from a first position outside of the patient to a second position within the abdominal cavity while the first portion of the bag body is disposed within the abdominal cavity.

In some embodiments, an end of the member is positionable outside of the patient while the first portion of the bag body is disposed within the abdominal cavity.

In certain embodiments, the viewing window is positioned along a wall of the first portion of the bag body.

In some embodiments, the member defines an opening that is positionable outside of the patient while the first portion of the bag body is disposed within the abdominal cavity.

In certain embodiments, the member and the viewing window together isolate the tissue visualization device from the loose tissue specimen and from the abdominal cavity.

In some embodiments, the tissue containment system further includes an access cap configured to close the opening of the bag body, the access cap including an entry port through which a tissue removal device can be passed to access the interior region of the bag body.

In certain embodiments, the tissue containment system further includes a wound liner that is configured to surround the second portion of the bag body.

In some embodiments, the access cap is configured to be secured to the wound liner in an airtight manner.

In certain embodiments, the tissue containment system further includes a bag introducer configured to introduce the bag body into the abdominal cavity.

In some embodiments, the entry port for the tissue removal device provides a passageway for the bag introducer.

In certain embodiments, the tissue removal device is a morcellator.

In some embodiments, the tissue visualization device is an endoscope.

In another aspect, a tissue containment system includes a containment bag configured to be placed in an abdominal cavity of a patient. The containment bag defines a main portion sized to contain a loose tissue specimen within the abdominal cavity, a first portion providing an opening sized to receive the loose tissue specimen and arranged to extend from the main portion outside of the patient while the main portion is disposed within the abdominal cavity, and a second portion arranged to extend from the main portion outside of the patient while the main portion is disposed within the abdominal cavity and providing a sealable end configured to receive a tissue visualization device at a location outside of the patient. The tissue containment system further includes a sealable connector attached to the sealable end of the second portion and through which the tissue visualization device can be passed to view an interior region of the containment bag.

Embodiments may provide one or more of the following advantages.

In some embodiments, the containment bag defines a main portion sized to hold and surround the tissue, an open-ended portion by which the main portion can be accessed with surgical instruments, and a closed-ended portion by which an interior region of the specimen container can be viewed with a tissue visualization device. The open-ended portion can provide a single opening (i.e., the only opening) of the containment bag.

In certain embodiments, the closed-ended portion has a preformed shape (e.g., a tubular shape) that projects from the main portion to facilitate positioning of the closed-ended portion within the wound. The closed-ended portion also defines a position of the viewing window along the containment bag such that contact between the viewing window and a tissue visualization device provides a tactile indication of an orientation and a position of the containment bag within the abdominal cavity. Because the closed-ended portion is sized and shaped to extend through the wound outside of the patient, the closed-ended portion can accommodate an inverted placement of the viewing window within the interior region of the containment bag.

In some embodiments, the viewing window has an unobstructed wall (e.g., without interior seam lines) that is impenetrable to engaging laparoscopic devices. The viewing window also provides the tissue containment system with an access port (e.g., a vision access port) that is separate from the access cap such that a region in which a tissue visualization device (e.g., an endoscope or laparoscope) is placed is out of the way of a region that may contain other surgical tools. The viewing window provides an optically clear barrier between the tissue visualization device and the interior of the containment bag. For example, the inner end region of the viewing window may be the only portion of the tissue containment system that separates a distal end of the tissue visualization device from the interior region of the containment bag. Accordingly, fogging of the tissue visualization device that may otherwise occur as a result of exposure to an interior region of the containment bag is prevented or minimized.

In certain embodiments, the retainer ring serves to fix a position of the closed-ended portion within a wound within the abdominal wall. The retainer ring is a compressible structure that can be compressed to pass through the wound and that can expand to a nominal configuration upon removal of an applied compression force to retain the closed-ended portion outside of the patient. Accordingly, the retainer ring locates the closed-ended portion of the containment bag with respect to the wound such that the viewing window extends from the abdominal wall for easy access by a tissue visualization device. The retainer ring may also be compressed in a packaging configuration within a bag introducer.

In some embodiments, the tissue visualization device remains isolated from the abdominal cavity when the tissue visualization device is inserted within the viewing window and moved down into the abdominal cavity. Inserted through the wound, the tissue visualization device has significant, improved 3D mobility to view the abdominal cavity, as compared to use with conventional containment bags that require use of a tissue visualization device with a trocar to maintain insufflation, but which also limits the degrees of freedom of the tissue visualization device. Because the tissue visualization device is withdrawn through the inverted configuration of the closed-ended portion of the containment bag, the tissue visualization device is isolated from the abdominal cavity and from the abdominal wall and thereby prevented from potentially contaminating the abdominal cavity. Additionally, since the viewing window provides a closed port of the containment bag, the containment bag does not have a second opening that would otherwise require an additional procedural step of closing such an opening to seal the containment bag. Therefore, the configuration of the viewing window reduces the risk of exposing a patient to a contaminated opening.

In some embodiments, the containment bag provides a degree of thermal insulation for the interior region of the containment bag within the abdominal cavity, such that the containment bag can be inflated with a gas that has a different temperature (e.g., that is significantly warmer) than a $CO_2$ insufflation temperature within the abdominal cavity. The isolated, spacious environment of the inflated containment bag increases control of the morcellation environment. For instance, owing to a separation of the interior region of the containment bag from the abdominal cavity, any potential fogging of the tissue visualization device (e.g., in contact with the viewing window) can be prevented or minimized.

Additionally, the constituency and warmer temperature of the gas delivered to the containment bag may provide an internal environment of the containment bag that is drier than the environment of the surrounding abdominal cavity, which can aid the start of a desiccation process on the tissue and other wet contents within the containment bag.

In certain embodiments, the access cap is constructed to interface with the open-ended region of the containment bag and the wound liner to close the opening of the containment bag outside of the abdominal wall of the patient. The access cap includes a cover plate that is sized to cover the opening of the containment bag. A snap-on configuration of the cover plate that is formed to interface directly with the wound liner provides a relatively simple, easy mechanism for covering the wound.

Other aspects, features, and advantages will be apparent from the description, the drawings, and the claims.

DETAILED DESCRIPTION

Figure 1:
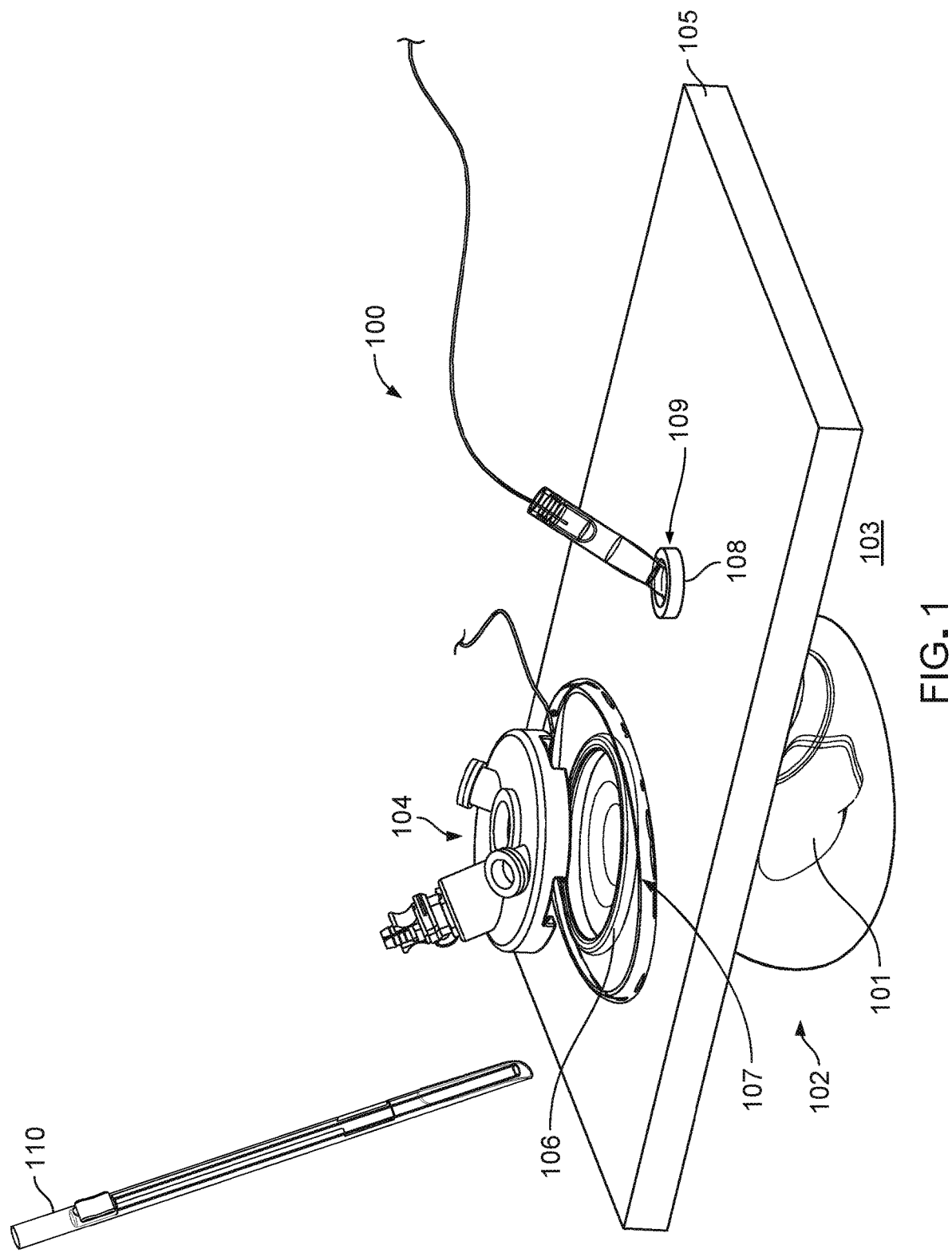
FIG. 1 is an exploded perspective view of a tissue containment system interfaced with an abdomen of a patient.
Figure 2:
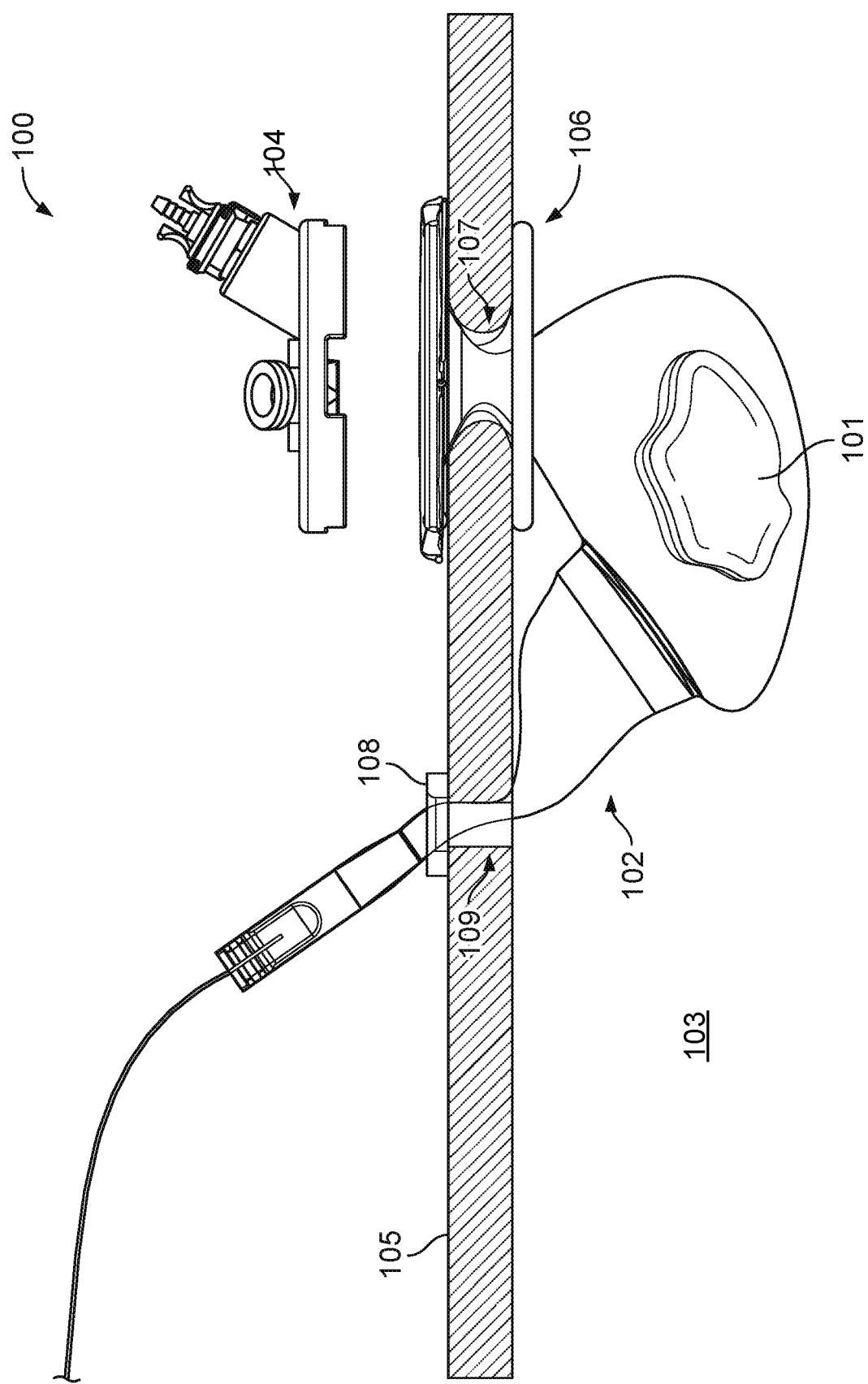
FIG. 2 is an exploded side view of a portion of the tissue containment system of FIG. 1.

FIGS. 1 and 2 illustrate a tissue containment system 100 (e.g., a morcellation containment system) that can provide an isolated environment in which a tissue 101 that has been separated from a structure within an abdominal cavity 103 of a patient can be morcellated or otherwise reduced and removed during a laparoscopic procedure. Example tissues 101 that may be loosed within the abdominal cavity 103 and morcellated within the tissue containment system 100 include tissues that are suspected of being pathological, but non-malignant, such as uterine fibroids, and endometriotic lesions. In a rare case that a tissue 101 proves to be malignant following the laparoscopic procedure, trace parts of the tissue 101 generated by the morcellation process will have been contained within the tissue containment system 100 and thereby isolated from the abdominal cavity 103. Example structures within the abdominal cavity 103 from which the tissue 101 may be separated include organs (e.g., a uterus or an ovary) and other structures. The tissue 101 may be separated from the abdominal structure or some other structure within the abdominal cavity by severance (e.g., cutting), ablation, or other energy sources (e.g., laser sources, electrocautery sources, harmonic sources, and bimodal energy sources). The tissue containment system 100 is constructed to interface with an abdominal wall 105 of the patient and is a disposable system that is discarded upon completion of the laparoscopic procedure.

The tissue containment system 100 includes a specimen container 102 that can be placed within the abdominal cavity 103, an access cap 104 formed to close the specimen container 102 along an external surface of the abdominal wall 105, a wound liner 106 (e.g., a wound protector) by which a portion of the specimen container 102 can be passed through a wound 107 (e.g., an incision) in the abdominal wall 105, and a bag introducer 110 by which the specimen container 102 can be placed within the abdominal cavity 103. The various components of the tissue containment system 100 may be provided as a kit of separate components that can be interfaced with each other and with the patient at the time of performing the laparoscopic procedure.

Figure 3:
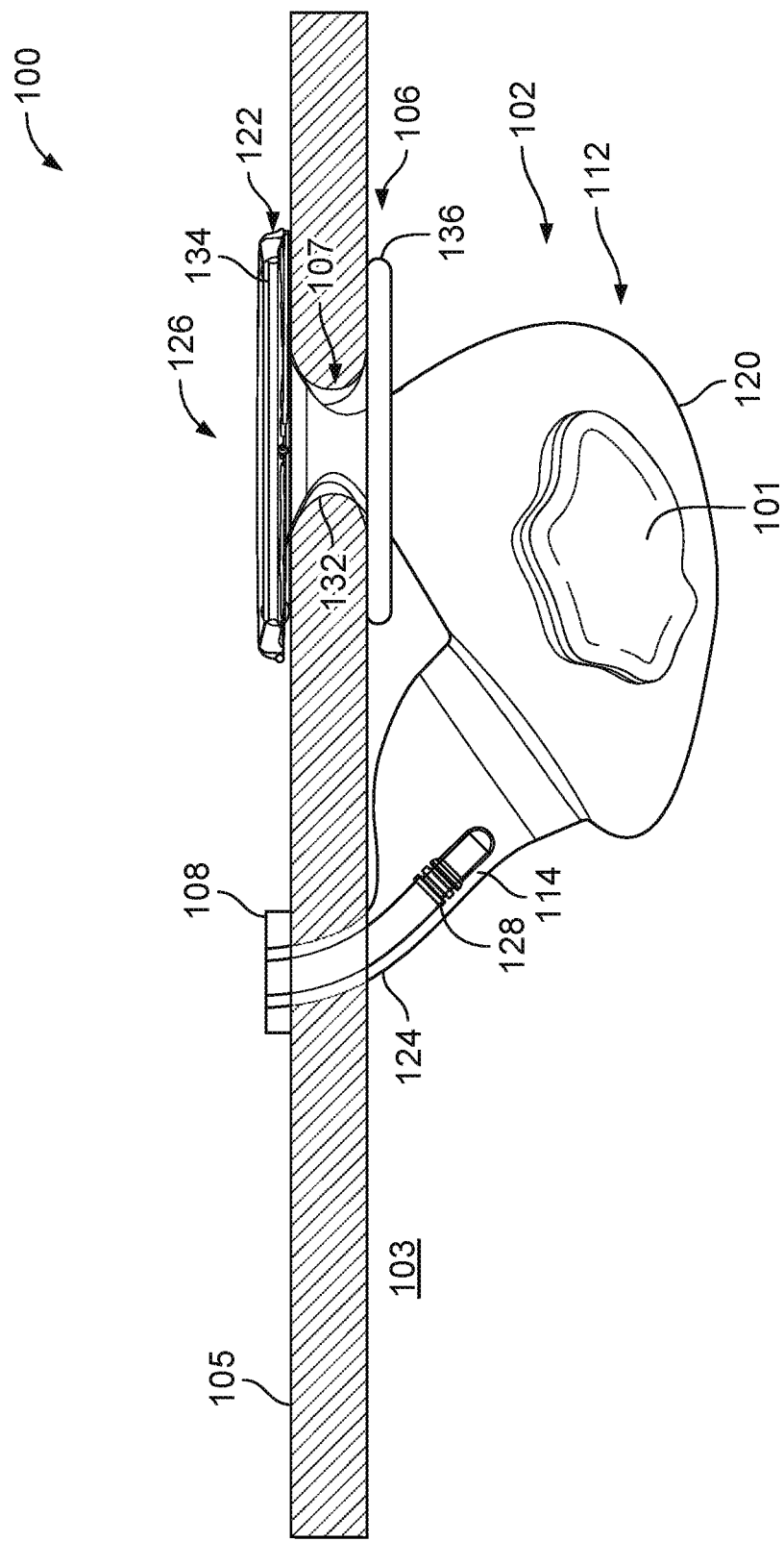
FIG. 3 is a side view of a portion of the tissue containment system of FIG. 1, shown with an inverted configuration of a containment bag.
Figure 4:
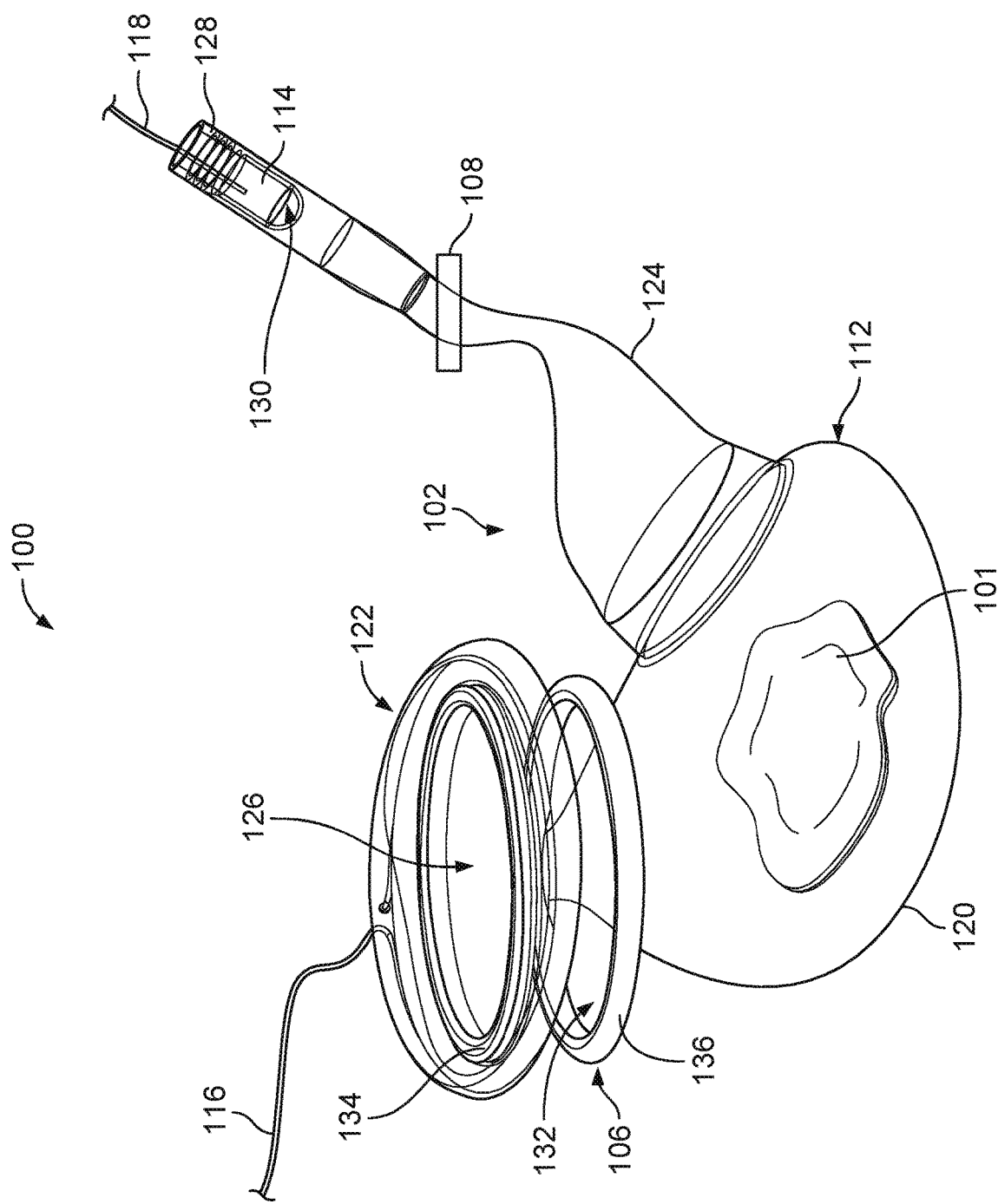
FIG. 4 is a perspective view of a wound liner of the tissue containment system of FIG. 1 and the containment bag, including a viewing window.

Referring to FIGS. 3 and 4, the specimen container 102 is generally shaped like a kidney and includes a containment bag 112, a viewing window 114, a retainer ring 108, a drawstring tether 116, and a pull tether 118. The containment bag 112 defines a main portion 120 (e.g., a central, largest volumetric portion) sized to hold and surround the tissue 101, an open-ended portion 122 by which the main portion 120 can be accessed with surgical instruments, and a closed-ended portion 124 by which an interior region of the specimen container 102 can be viewed with a tissue visualization device (e.g., an endoscope or a disposable visualization device). The main portion 120, the open-ended portion 122, and the closed-ended portion 124 are in fluid communication with one another. The open-ended portion 122 provides a single opening (i.e., the sole opening) 26 of the specimen container 102. The open-ended portion 122 is sized and shaped to receive the tissue 101 within the abdominal cavity 103 during one stage of the procedure and to interface with the access cap 104 along the external surface of the abdominal wall 105 during a later stage of the procedure. The opening 126 of the specimen container 102 is lined with the drawstring tether 116, by which the opening 126 can be closed (e.g., cinched) upon completion of the laparoscopic procedure. The drawstring tether 116 can also be used to pull the open-ended portion 122 up through the wound liner 106 and out of the patient so that a position of the open-ended portion 122 of the containment bag 112 can be fixed between the access cap 104 and the wound liner 106, as will be discussed in more detail below with respect to FIGS. 8-14.

The retainer ring 108 surrounds the closed-ended portion 124 of the containment bag 112 and serves to fix a position of the closed-ended portion 124 within a wound 109 (e.g., an incision) within the abdominal wall 105. The retainer ring 108 is a compressible structure that can be compressed to allow it to be passed through the wound 109 and that can expand to a nominal configuration (e.g., as shown in FIGS. 1-5) upon removal of an applied compression force. The expanded or nominal configuration of the retainer ring 108 can help to ensure that the retainer ring 108 remains outside the patient during tissue morcellation.

The closed-ended portion 124 has a preformed shape that projects from the main portion 120 to facilitate positioning of the closed-ended portion 124 within the wound 109. The closed-ended portion 124 also defines a position of the viewing window 114 along the containment bag 112 such that contact between the viewing window 114 and a tissue visualization device provides a tactile indication of an orientation and a position of the containment bag 112 within the abdominal cavity 103. Because the closed-ended portion 124 is sized and shaped to extend through the wound 109 outside of the patient, the closed-ended portion 124 can accommodate an inverted placement of the viewing window 114 within the interior region of the specimen container 102, as shown in FIG. 3. The viewing window 114 is clear, has a U shaped cross-section, and is sized and shaped to receive a distal end of a tissue visualization device directly (e.g., without a trocar) for viewing the interior region of the specimen container 102. The viewing window 114 is a rigid structure (e.g., as compared to the containment bag 112) that has an unobstructed wall (e.g., without interior seam lines) that is impenetrable to engaging laparoscopic devices during normal use. The viewing window 114 provides the tissue containment system 100 with an access port (e.g., a vision access port) that is separate from the access cap 104 such that a region in which a tissue visualization device is placed is out of the way of a region that may contain other surgical tools. The pull tether 118 is attached to the closed-ended portion 124 and can be used to pull the closed-ended portion 124 (e.g., including the retainer ring 108) through the wound 109 and outside of the patient.

The containment bag 112 is a compliant structure that can be flattened, rolled, and/or folded in a packaging configuration (e.g., within the bag introducer 110), inflated to achieve a predetermined, expanded shape (e.g., the general shape of a kidney, as shown in FIGS. 1-4) for morcellation of the tissue 101 therein, and allowed to deflate to achieve a less formed, collapsed configuration for removal of the specimen container 102 from the abdominal cavity 103 through the wound liner 106, as will be discussed in more detail below with respect to FIGS. 8-14. The containment bag 112 is impermeable to liquids and gases such that once the open end 126 is positioned outside of the abdominal wall 105, the tissue 101 contained therein is isolated from the abdominal cavity 103 of the patient. The impermeable character of the containment bag 112 further prevents leakage of an inflation gas within the containment bag 112 to the abdominal cavity 103, as will be discussed in more detail below with respect to FIGS. 8-14.

The containment bag 112 is relatively puncture resistant, such that any potential of the containment bag 112 being pierced by a sharp edge of the morcellator or another laparoscopic device is minimized should the sharp edge inadvertently contact the containment bag 112. Furthermore, the containment bag 112 defines an interior region that is separated from (e.g., physically and, to some degree, thermally) the abdominal cavity 103, such that the containment bag 112 can be inflated with a gas (e.g., filtered air) of a temperature that is different (e.g., warmer) than a temperature of $CO_2$ insufflation gas within the abdominal cavity 103. For instance, in some examples, the abdominal cavity 103 may be insufflated with medical grade $CO_2$ at an ambient room temperature in a range of about 19° C. to about 21° C., and the containment bag 112 may be inflated with air at a temperature in a range of about 19° C. up to typical body temperature (e.g., about 37° C.). The containment bag 112 is translucent such that although the containment bag 112 is not optically clear, some light can pass through the containment bag 112, which may facilitate imaging of the interior region of the containment bag 112.

The containment bag 112 is made of one or more materials that are compliant, impermeable, puncture resistant, and translucent, as described above. Example materials from which the containment bag 112 can be made include polyurethane, ballistic nylon, and ripstop nylon. The containment bag 112 may be formed from one or more sheets of material that are sealed along one or more peripheral edges, excluding the opening 126. Edges of the one or more sheets of material may be sealed via heat stake, gluing, or ultrasonic attachment.

In an inflated state, the containment bag 112 provides a large, safe working zone in which the tissue 101 can be morcellated within the containment bag 112 at a location remote (e.g., spaced apart) from organs in the abdominal cavity 103. The containment bag 112 is also small enough to avoid significant infolding or double layering of the containment bag 112 within the abdominal cavity 103. The containment bag 112 can have a volume that is greater than a nominal volume of an abdominal cavity in which it is deployed. For example, an abdominal cavity may have a nominal volume in a range of about 4 L to about 6 L. However, in a fully inflated state (and positioned within a patient, as shown in FIG. 1), the containment bag 112 typically has a volume of about 6 L to about 8 L, and the main portion 120 of the containment bag 112 typically has a volume of about 5.5 L to about 7.5 L.

The main portion 120 typically has a nominal (e.g., collapsed, flattened) length of about 30 cm to about 40 cm (e.g., about 35 cm) and a nominal width of about 18 cm to about 24 cm (e.g., about 21 cm). In an inflated state, the open-ended portion 122 is generally cylindrically shaped, and the open end 126 typically has a diameter of about 12 cm to about 24 cm (e.g., about 18 cm). The open-ended portion 122 typically has a nominal length of about 12 cm to about 20 cm (e.g., about 16 cm) and a nominal width of about 12 cm to about 15 cm (e.g., about 14 cm). In an inflated state, the closed-ended portion 124 has a generally tubular shape. The closed-ended portion 124 typically has a nominal length of about 20 cm to about 50 cm (e.g., about 35 cm), an interior (e.g., adjacent the main portion 120) nominal width of about 6 cm to about 10 cm (e.g., about 8 cm), and a peripheral nominal width (e.g., adjacent a rim 128 of the viewing window 114) of about 1.0 cm to about 1.5 cm (e.g., about 1.2 cm). The closed-ended portion 124 typically extends about 20 cm to about 45 cm outside of the abdominal wall 105 during a laparoscopic procedure.

The tethers 116, 118 are typically made of one or more materials including nylon, tetrafluoroethylene (TFE), and flashspun high-density polyethylene fibers. The tethers 116, 118 typically have a length of about 30 cm to about 50 cm (e.g., about 40 cm). The retainer ring 108 has a nominal internal diameter that is two to four times larger than a length of the wound 109. For example, the wound 109 typically has a length in a range of about 20 mm to about 25 mm, and the retainer ring 108 typically has a nominal internal diameter of about 3.0 cm to about 3.5 cm (e.g., about 3.0 cm). The retainer ring 108 is attached to the closed-ended portion 124 of the containment bag 112 via heat sealing, glue, or ultrasonic attachment. The retainer ring 108 may be made of one or more soft, expandable or compressible materials that allow the retainer ring 108 to pass through the wound 109, such as foam, polypropylene, TPE, polyethylene, or santoprene.

The viewing window 114 provides an optically clear barrier between the tissue visualization device and the containment bag 112. The viewing window 114 is attached along the rim 128 to the closed-ended portion 124 of the containment bag 112 in a manner such that an inner end region 130 of the viewing window 114 is free from (e.g., not attached to) the containment bag 112. Accordingly, the inner end region 130 of the viewing window 114 is the only portion of the tissue containment system 100 that may separate a distal end of the tissue visualization device from the interior region of the containment bag 112. The viewing window 114 is typically attached to the closed-ended portion 124 of the containment bag 112 via an airtight seal (e.g., a hermetic seal), such as a heat seal, an ultrasonic weld, or one or more mechanical means (e.g., an o-ring, a nut, etc.). In this manner, the viewing window 114 provides a seal between an interior region of the containment bag 112 and an ambient room environment in which the laparoscopic procedure is performed. The viewing window 114 is typically made of one or more clear plastic materials, such as polycarbonate or other optically clear materials. The viewing window 114 typically has a length of about 2.0 cm to about 4.0 cm (e.g., about 3.0 cm) and an internal rim diameter of about 1.0 cm to about 1.5 cm (e.g., about 1.2 cm).

Still referring to FIGS. 3 and 4, the wound liner 106 provides an extended passageway through the wound 107 and an enlarged exit region near the internal surface of the abdominal wall 105 for the open-ended portion 122 of the containment bag 112 and thereby protects the wound 107 from mechanical wear of the containment bag 112 and potential tissue contamination that may be present thereon near the opening 126 of the containment bag 112. The wound liner 106 is generally cylindrically shaped and includes a collapsible wall 132 that can be passed though the wound 107, a port access ring 134 attached to one end of the collapsible wall 132, and an anchoring ring 136 attached to an opposite end of the collapsible wall 132.

The collapsible wall 132 is a compliant structure that can be collapsed for insertion of the anchoring ring 136 through the wound 107 and that can be extended from the collapsed configuration to position the port access ring 134 against the external surface of the abdominal wall 105 with the anchoring ring 136 positioned within the abdominal cavity 103 (e.g. abutting an internal surface of the abdominal wall 105 or hanging spaced apart from the internal surface of the abdominal wall 105). The collapsible wall 132 may have the same material formulation as the containment bag 112 and therefore may be impermeable, puncture resistant, and translucent, as discussed above with respect to the containment bag 112. The collapsible wall 132 typically has a maximum extended length of about 12 cm to about 16 cm (e.g., about 14 cm) and an internal diameter of about 8 cm to about 12 cm (e.g., about 10 cm). The collapsible wall 132 is typically sealed to itself along its ends snuggly about the port access ring 134 and the anchoring ring 136.

The port access ring 134 may have a rectangular (e.g., square) cross-sectional shape and has a flexibility that allows the port access ring 134 to be snap fit into engagement with the access cap 104, as will be discussed in more detail below with respect to FIGS. 8-14. The anchoring ring 136 may have a circular cross-sectional shape and has a flexibility that allows the anchoring ring 136 to be squeezed for inserting through the wound 107, as will be discussed in more detail below with respect to FIGS. 8-14. The port access ring 134 and the anchoring ring 136 typically have an internal diameter that is about equal to the internal diameter of the collapsible wall 132.

Figure 5:
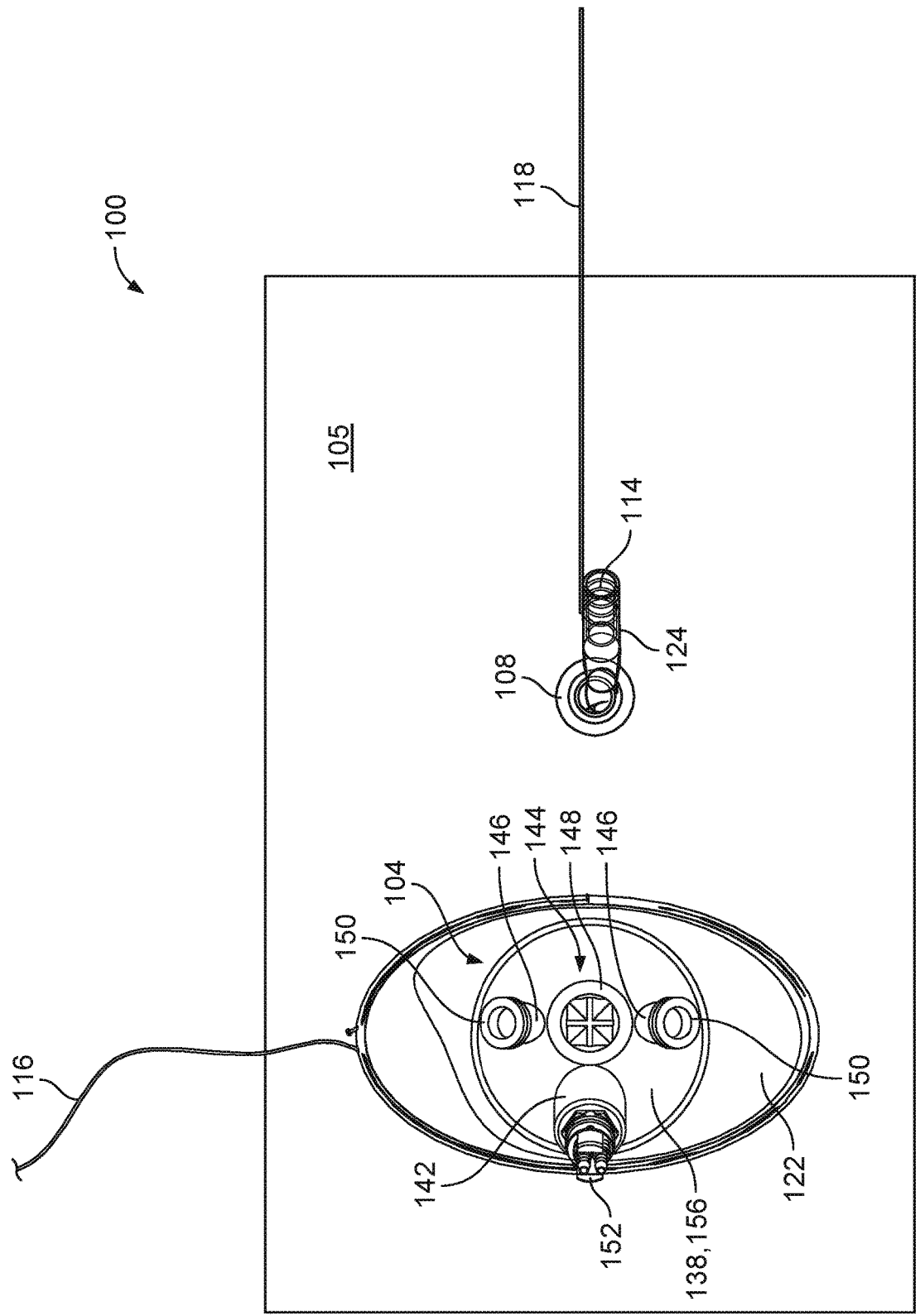
FIG. 5 is a perspective view of a portion of the tissue containment system of FIG. 1.
Figure 6:
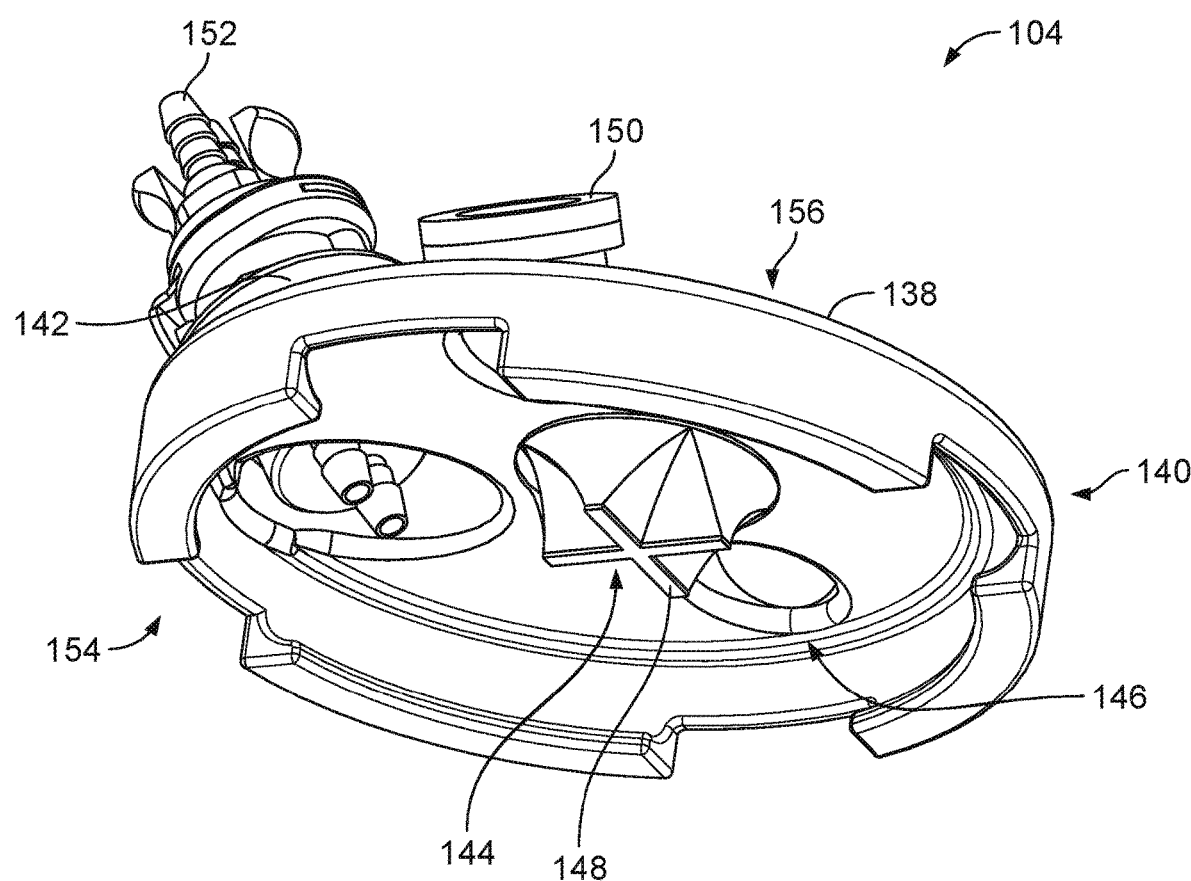
FIG. 6 is a perspective view of an access cap of the tissue containment system of FIG. 1.

Referring to FIGS. 5 and 6, the access cap 104 is constructed to interface with the open-ended portion 122 of the containment bag 112 and the wound liner 106 to close the opening 126 of the containment bag 112 outside of the abdominal wall 105 of the patient. The access cap 104 includes a cover plate 138 that is sized to cover the opening 126 of the containment bag 112. The cover plate 138 defines a flat upper wall 156, a peripheral flange 140 into which the port access ring 134 of the wound liner 106 can be snapped fitted, an insufflation port 142 for connection to a gas line, a morcellation port 144 that allows passage of a morcellator shaft and the bag introducer 110, and two working ports 146 that allow passage of other laparoscopic tools, such as a dissector, a grasper, an irrigation line, a scope/camera. The access cap 104 further includes valves 148, 150 and a quick connect fitting 152 that are respectively secured to the morcellation port 144, the working ports 146, and the insufflation port 142. The valves 148, 150 (e.g., cross-slit valves, duck bill valves, or other mechanically activated valves) can secure instruments passing therethrough while allowing passage of only minimal gas leakage out of the containment bag 112. The quick connect fitting 152 can secure a gas line (e.g., a dual-lumen gas line) that can deliver and/or withdraw gas from the containment bag 112. For example, such a gas line may include a first lumen that delivers an inflation gas (e.g., medical grade $CO_2$) into the containment bag 112 and a second lumen that withdraws smoke (e.g., produced during power morcellation) out of the containment bag 112.

The cover plate 138 is generally circular and has a diameter that is three to four times larger than a length of the wound 107. For example, the wound 107 typically has a length in a range of about 20 mm to about 25 mm, and the cover plate 138 typically has a diameter of about 7 cm to about 12 cm (e.g., about 10 cm). The peripheral flange 140 of the cover plate 138 is a lipped structure that forms a receptacle and defines multiple notches 154 that facilitate snap fitting of the port access ring 134 into the peripheral flange 140. A snap-on configuration of the cover plate 138 that is formed to interface directly with the wound liner 106 provides a relatively simple, easy mechanism for covering the wound 109, as compared to certain conventional caps. The cover plate 138 may be a rigid, flexible, or semi-rigid structure that is typically made of one or more materials, such as santoprene, EPDM (ethylene propylene diene monomer), polypropylene, nylon, polycarbonate, polyethylene, acrylonitrile butadiene styrene (ABS), polyetherimide (PEI), or other engineering injection medical grade resins. The cover plate 138 may be manufactured using one or more techniques, such as machining or injection molding. The valves 148, 150 are typically made of one or more flexible materials, such as silicone. The quick connect fitting 152 is a rigid connection that is typically made of one or more sufficiently rigid materials.

Figure 7:
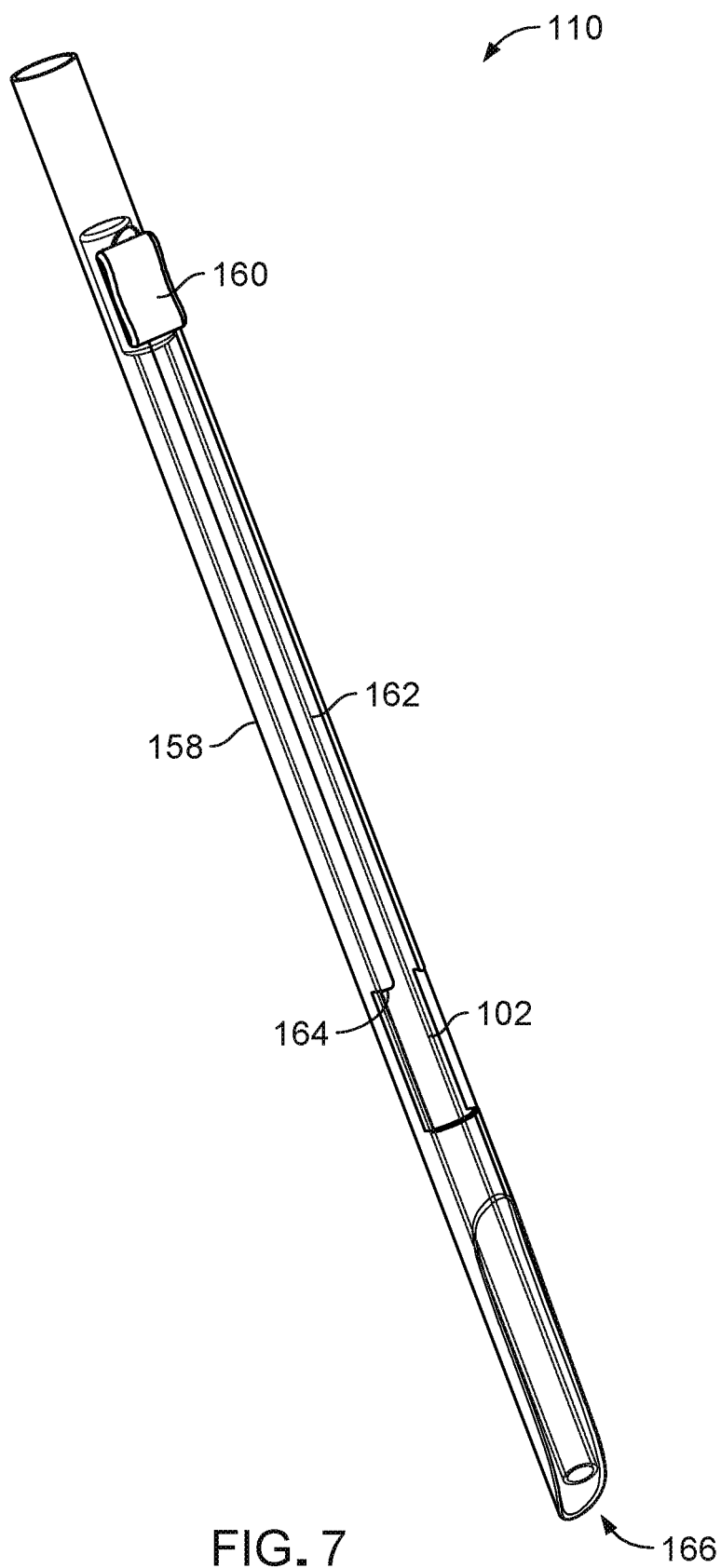
FIG. 7 is a perspective view of a bag introducer of the tissue containment system of FIG. 1.

Referring to FIG. 7, the bag introducer 110 includes a shaft 158 that is sized to accommodate the specimen container 102, including the containment bag 112 and the viewing window 114 and the retainer ring 108 (omitted from FIG. 7 for clarity) in a rolled or folded configuration and a slidable button 160 by which the specimen container 102 can be ejected from the shaft 158. The shaft 158 defines a slot 162 along which the slidable button 160 can be translated distally to move the specimen container 102 and a notch 164 that can receive the slidable button 160 to terminate distal movement of the slidable button 160. The shaft 158 also defines a distal opening 166 from which the specimen container 102 can exit the shaft 158 as the slidable button 160 is moved distally along the shaft 158. The bag introducer 110 can be passed through the morcellation port 144 of the access cap 104 for insertion and deployment of the specimen container 102. The bag introducer 110 typically has a total length of about 15 cm to about 25 cm (e.g., about 20 cm) and an internal diameter of about 2 cm to about 3 cm (e.g., about 2.5 cm). The bag introducer 110 is a rigid structure that is typically made of one or more materials, such as polycarbonate or ABS.

Figure 8:
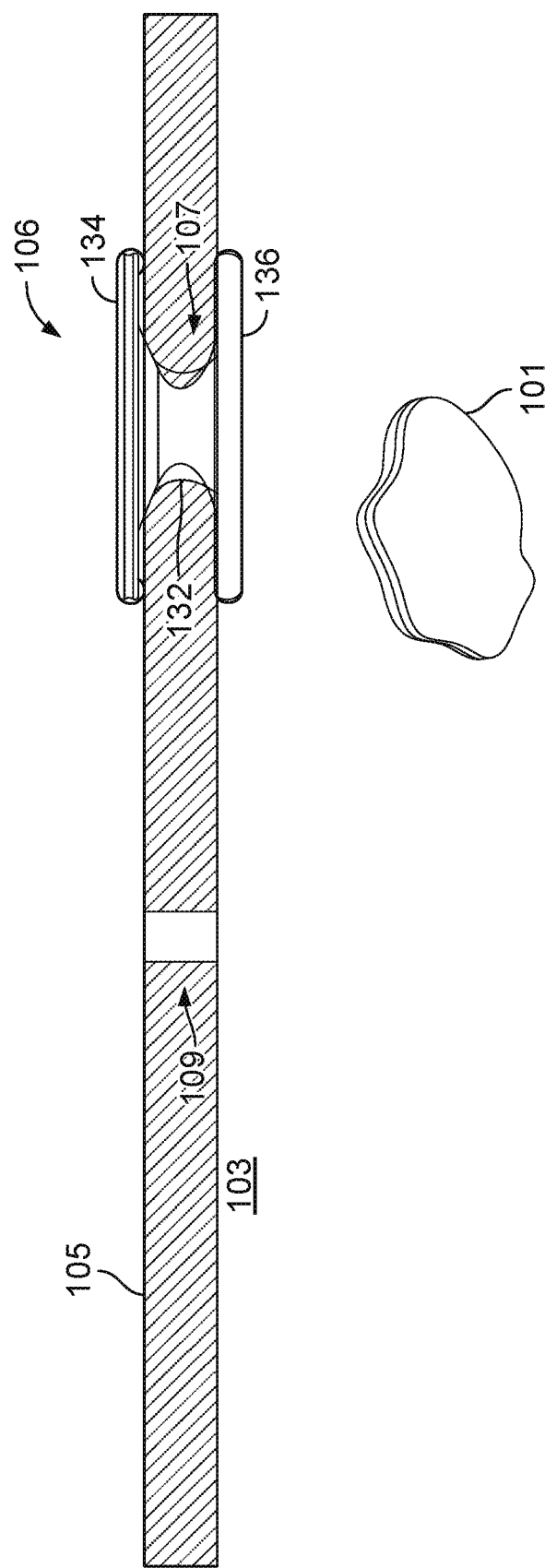
FIGS. 8-14 illustrate a method of using the tissue containment system of FIG. 1 during a laparoscopic procedure.

FIGS. 8-14 illustrate a method of containing (e.g., isolating) the tissue 101 using the tissue containment system 100 during a laparoscopic procedure. Referring to FIG. 8, the wound liner 106 is squeezed to a compact configuration and inserted within the wound 107. The anchoring ring 136 of the wound liner 106 is positioned within the abdominal cavity 103 and allowed to relax to a nominal state. The port access ring 134 of the wound liner 106 remains outside of the abdominal cavity 103 and is allowed to rest against the external surface of the abdominal wall 105 such that an entire extent of the wound 107 is protected by the wound liner 106.

Figure 9:
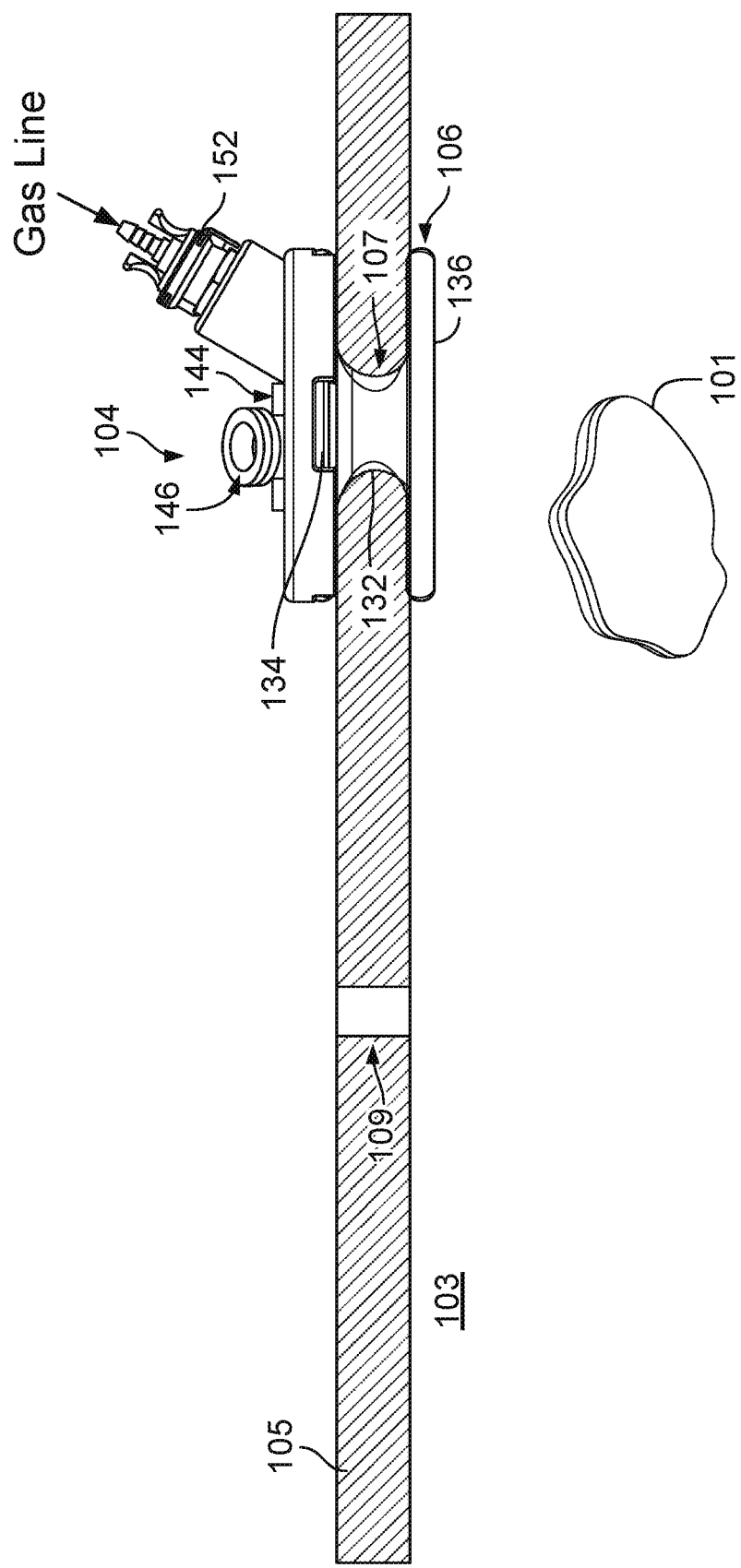

Referring to FIG. 9, the access cap 104 is snap fitted to the port access ring 134 of the wound liner 106 to seal the abdominal cavity 103. A gas line is connected to the quick connect fitting 152 at the insufflation port 142 of the access cap 104, and the abdominal cavity 103 is insufflated with a gas (e.g., medical grade $CO_2$) delivered from a delivery lumen of the gas line. The $CO_2$ gas temperature typically has an ambient room temperature of about 19° C. to about 21° C., which is relatively cold as compared to typical body temperature of about 37° C. The insufflation expands a volume of the abdominal cavity 103 to allow the specimen container 102 to be introduced into and deployed within the abdominal cavity 103.

Figure 10:
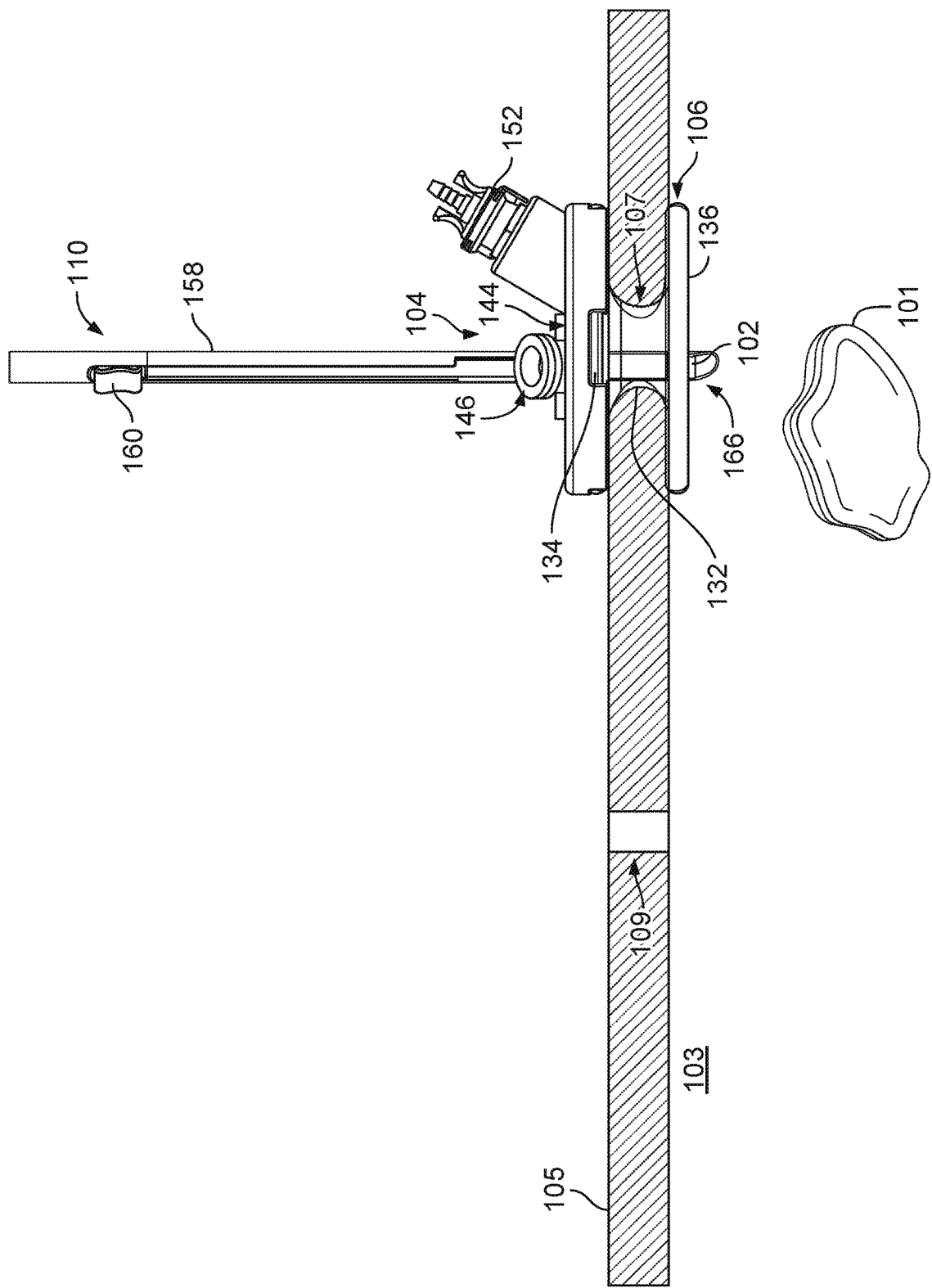

Referring to FIG. 10, the gas line is removed, and the bag introducer 110, loaded with the specimen container 102, is inserted into the morcellation port 144 of the access cap 104 until at least the distal opening 166 of the shaft 158 is positioned within the wound liner 106. The slidable button 160 is translated distally until the specimen container 102 is ejected from the shaft 158 and delivered to the abdominal cavity 103. The bag introducer 110 is removed (e.g., withdrawn) from the morcellation port 144, and one or more laparoscopic instruments (e.g., a grasper, clamps, or a robotic grasper) are inserted into the abdominal cavity 103 via the working ports 146 of the access cap 104.

Figure 11:
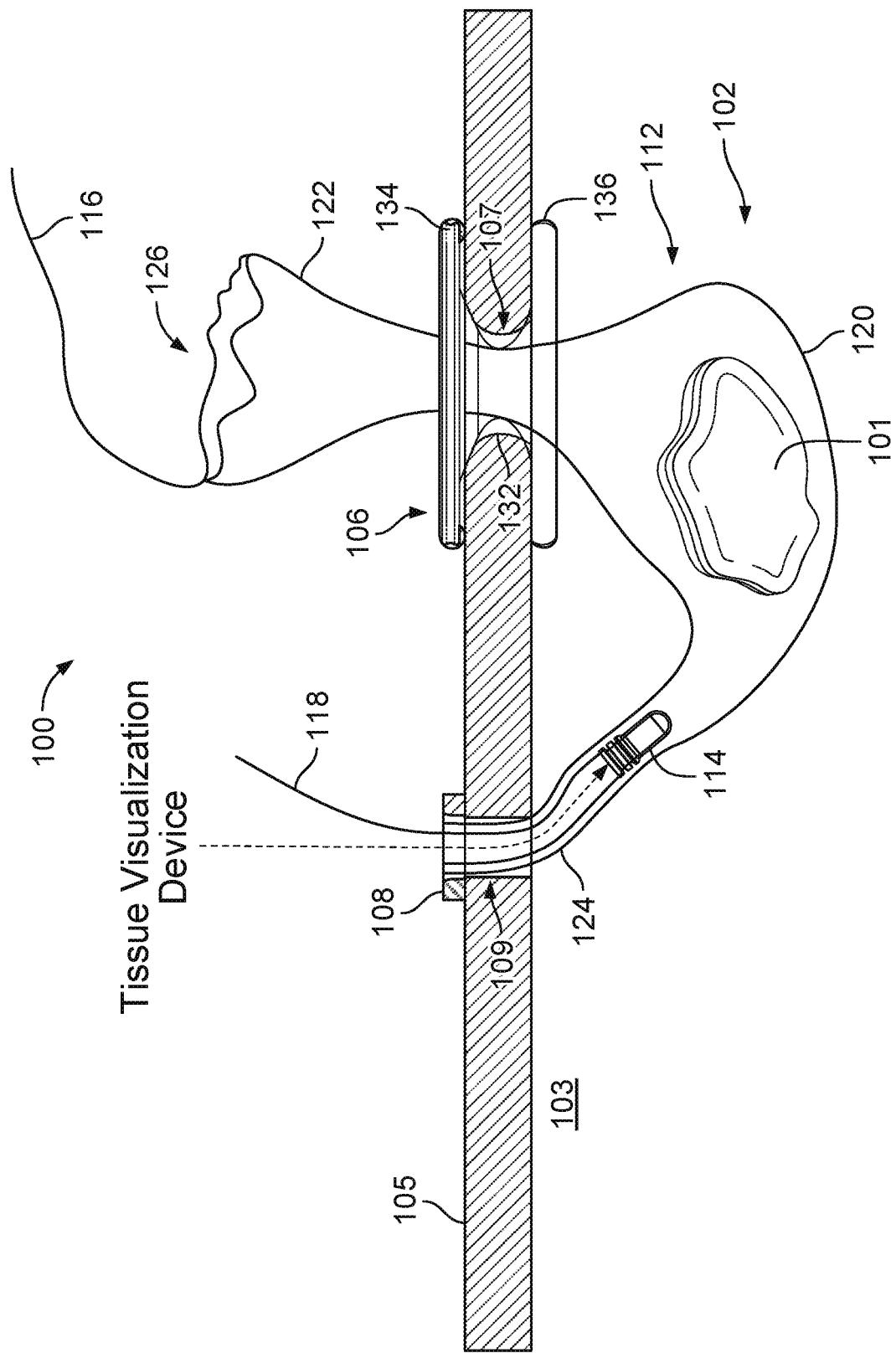

Referring to FIG. 11, the specimen container 102 is deployed (e.g., the containment bag 112 is unrolled, unfolded, and/or spread out), and the pull tether 118 is pulled through the wound 109 using the laparoscopic instruments. The pull tether 118 may be visualized by an endoscope positioned within a wound of the abdominal cavity 103 during an earlier stage of the surgery. The pull tether 118 is pulled until the retainer ring 108 of the specimen container 102 is positioned outside of the abdominal wall 105. Accordingly, the retainer ring 108 locates the closed-ended portion 124 of the containment bag 112 with respect to the wound 109 such that the viewing window 114 extends from the abdominal wall 105 for easy access by a tissue visualization device.

The tissue visualization device is inserted within the viewing window 114 and is moved down into the abdominal cavity 103 for visualization in a manner such that, due to a position of the retainer ring 108, the closed-ended portion 124 remains within the wound 109 in an inverted configuration, and the tissue visualization device remains isolated from the abdominal cavity 103. Inserted through the wound 109, the tissue visualization device has significant, improved 3D mobility to view the abdominal cavity 103, as compared to use with conventional containment bags that require use of a tissue visualization device with a trocar to maintain insufflation. Visualized by the tissue visualization device, the tissue 101 is placed within the containment bag 112 via the opening 126 of the containment bag 112. The drawstring tether 116 is then pulled into the wound liner 106 using the laparoscopic instruments. With the drawstring tether 116 disposed within the wound liner 106, the open-ended portion 122 of the containment bag 112 is positioned near the abdominal wall 105 for easy access. The access cap 104 is removed from the wound liner 106, and the open-ended portion 122 of the containment bag 112 is quickly pulled up through the wound liner 106 until the open-ended portion 122 overlays the port access ring 134 of the wound liner 106. The open-ended portion 122 is pulled quickly through the wound liner 106 to minimize the loss of pneumoperitoneum (e.g., abdominal gas pressure).

Figure 12:
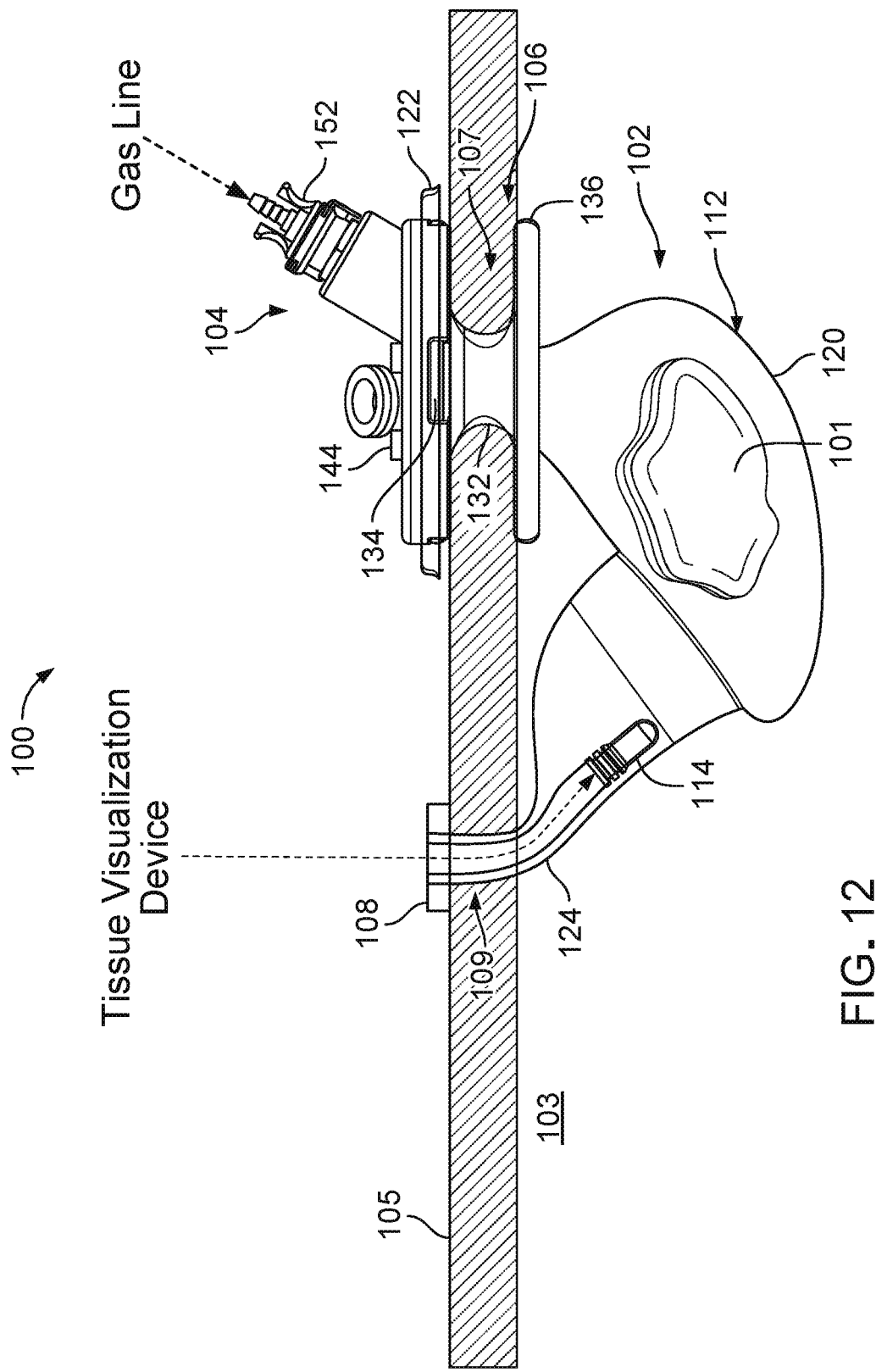

Referring to FIG. 12, the access cap 104 (e.g., with the gas line still attached to the quick connect fitting 152) is quickly reattached to the port access ring 134 (e.g., to minimize the loss of pneumoperitoneum) with the open-ended portion 122 of the containment bag 112 fixed (e.g., sandwiched) between the access cap 104 and the port access ring 134. The containment bag 112 is inflated (e.g., with filtered air or medical grade $CO_2$) via the delivery lumen of the gas line to make room in the containment bag 112 for insertion of a morcellator (e.g., a power morcellator). For example, the gas exerts forces on an internal surface of the containment bag 112 in a direction normal to the internal surface to expand (e.g., inflate) the containment bag 112 to create a working space needed for a morcellation process.

The isolated, spacious environment of the inflated containment bag 112 increases control of the morcellation environment. For instance, owing to heat transfer properties of the material of the containment bag 112, the temperature of the gas delivered to the containment bag 112 can be about the same (e.g., when the gas is medical grade $CO_2$) or warmer (e.g., when the gas is filtered air) than that of the abdominal insufflation gas such that any potential fogging of the tissue visualization device (e.g., in contact with the viewing window 114) is prevented or minimized. The temperature of $CO_2$ delivered to the containment bag 112 is typically in a range of about 19° C. to about 21° C., whereas the temperature of filtered air delivered to the containment bag 112 is typically in a range of about 19° C. to about 37° C. In some examples, the constituency and warmer temperature of filtered air delivered to the containment bag 112 may provide an internal environment of the containment bag 112 that is drier than the environment of the surrounding abdominal cavity 103, which can aid the start of a desiccation process on the tissue 101 and other wet contents within the containment bag 112. Isolating drier filtered air within the containment bag 112 from the abdominal cavity 103 may be advantageous, as peritoneal drying has been linked to post-operative pain and to evaporative cooling, which may decrease core temperature, increase intra-operative hypothermia, and promote adhesion formation. In some examples, the filtered air delivered to the containment bag 112 may be warmer and humidified. To the extent that any heat from filtered air within the containment bag 112 is transferred through the containment bag 112 to the abdominal cavity 103, such heat will tend to minimize undesirable effects associated with abdominal insufflation $CO_2$ that is colder than the body temperature.

Figure 13:
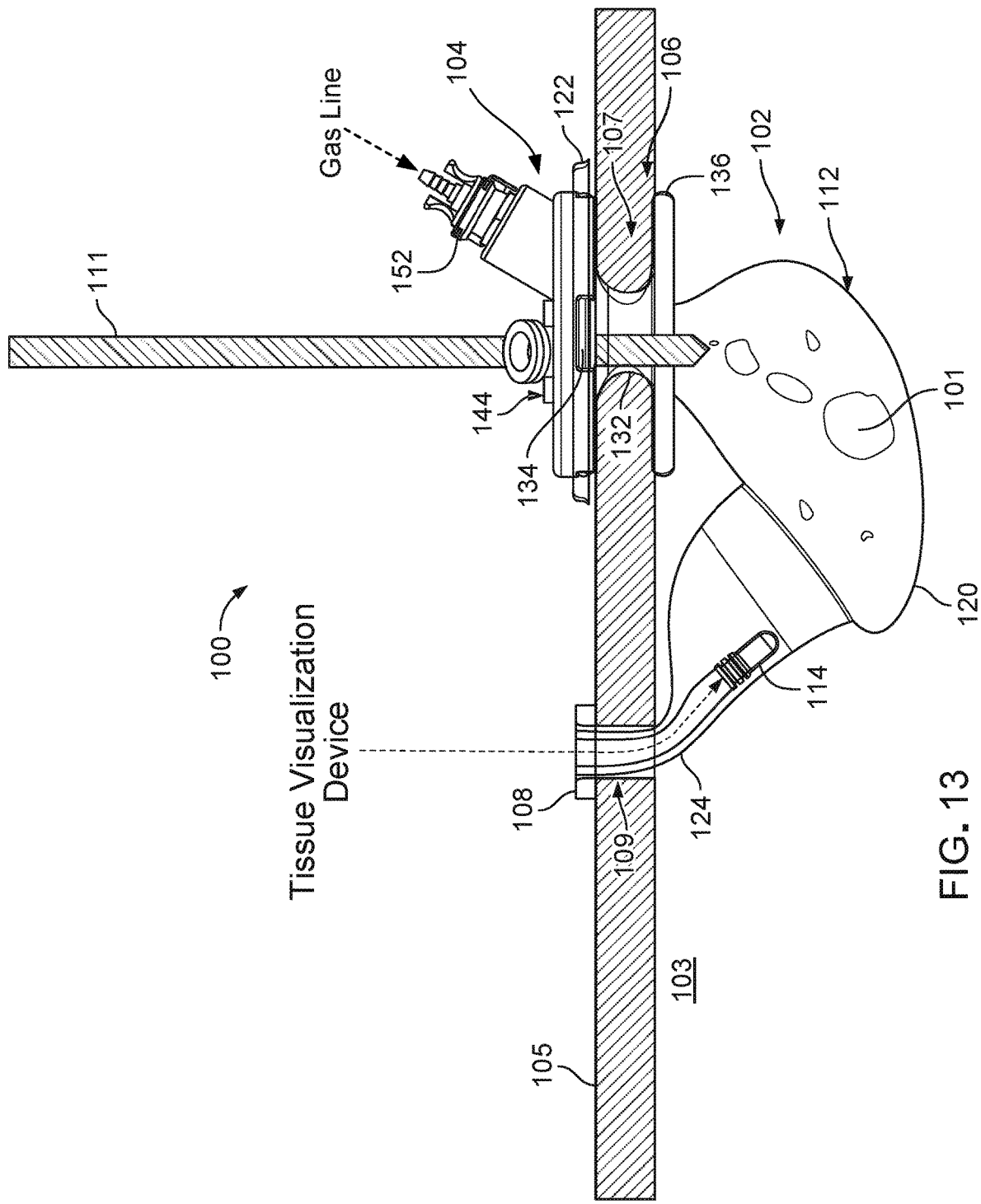

Referring to FIG. 13, once the containment bag 112 is inflated, a morcellator 111 is inserted into the containment bag 112 via the morcellation port 144 of the access cap 104 and used to morcellate the tissue 101. The morcellator 111 may be any suitable, commercially available tissue morcellator. The morcellation process is visualized with the tissue visualization device that is engaged with the viewing window 114 interior to the abdominal cavity 103, while the tissue visualization device is isolated from the abdominal cavity 103 and isolated from an interior region of the containment bag 112. During the morcellation process, the tissue 101 is ground into small pieces and withdrawn from the containment bag 112 (e.g., suctioned through the morcellator 111). Any trace amounts or particles of tissue generated during the morcellation process, but not suctioned through morcellator 111, are contained within the containment bag 112 and thus prevented from contacting (e.g., potentially contaminating) the abdominal cavity 103.

Figure 14:
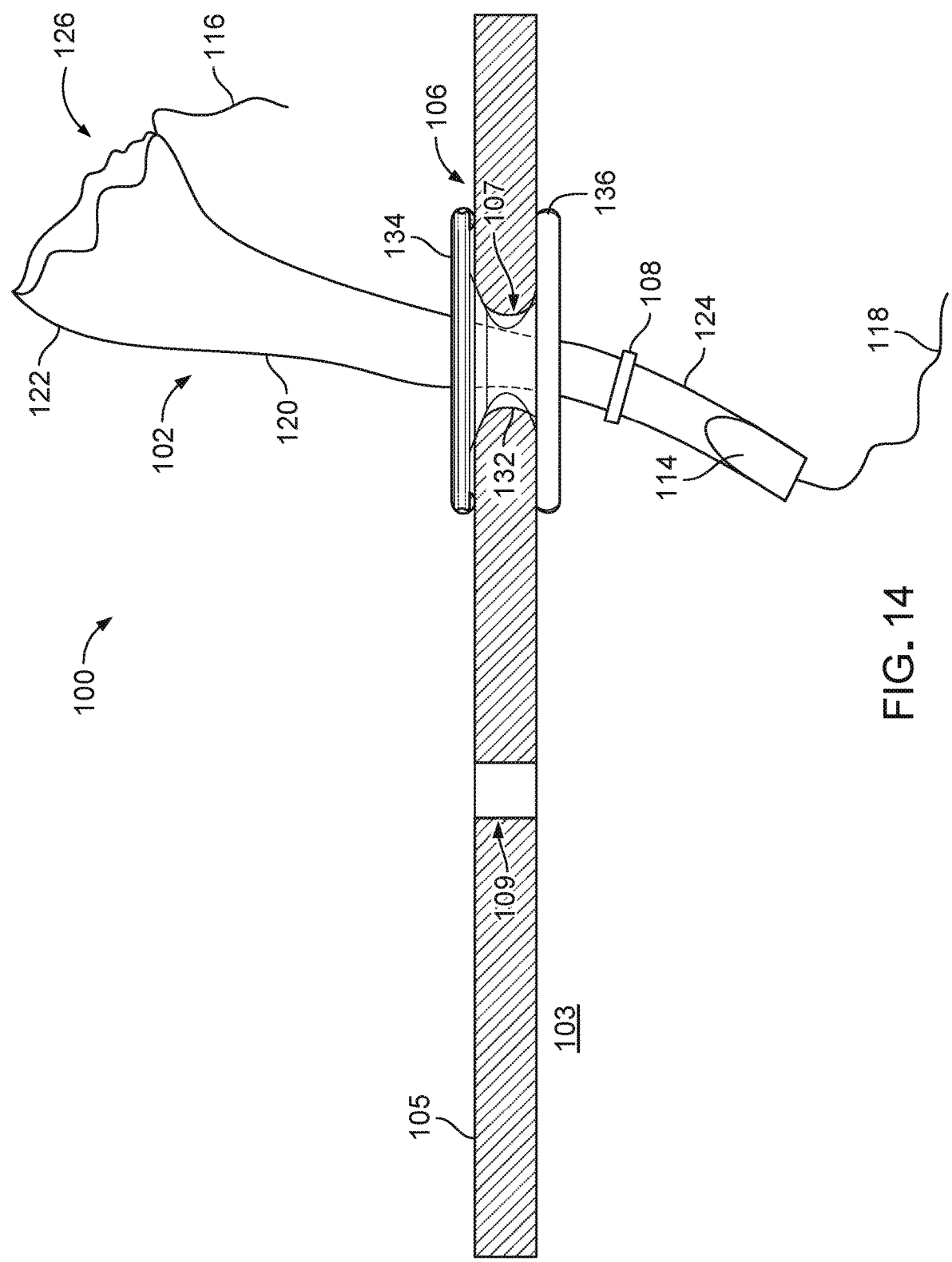

Referring to FIG. 14, upon completion of the morcellation process, the morcellator 111 is withdrawn from the morcellator port 144, and any other laparoscopic instruments that may still be disposed within the containment bag 112 are withdrawn from the working ports 146. After the morcellator 111 and laparoscopic instruments are removed, the tissue visualization device is removed from the wound 109. Because the tissue visualization device is withdrawn through the inverted configuration of the closed-ended portion 124 of the containment bag 112, the tissue visualization device is isolated from the abdominal cavity 103 and from the abdominal wall 105 and thereby prevented from potentially contaminating the abdominal cavity 103. Additionally, since the viewing window 114 provides a closed port of the containment bag 112, the containment bag 112 does not have a second opening that would otherwise exist in a conventional containment bag and therefore eliminates the need for an additional procedural step to close such an opening and eliminates a potential of exposing a patient to a contaminated opening. Once the tissue visualization device is removed from the patient, the retainer ring 108 is then pushed down into the abdominal cavity 103 through the wound 109. The access cap 104 is removed from the wound liner 106, and the open-ended portion 122 of the containment bag 112 is pulled through the wound liner 106 to remove the containment bag 112 from the abdominal cavity 103. The containment bag 112 can be knotted about itself, tied with the drawstring tether 116, or otherwise closed at the open-ended portion 122 and discarded.

Figure 15:
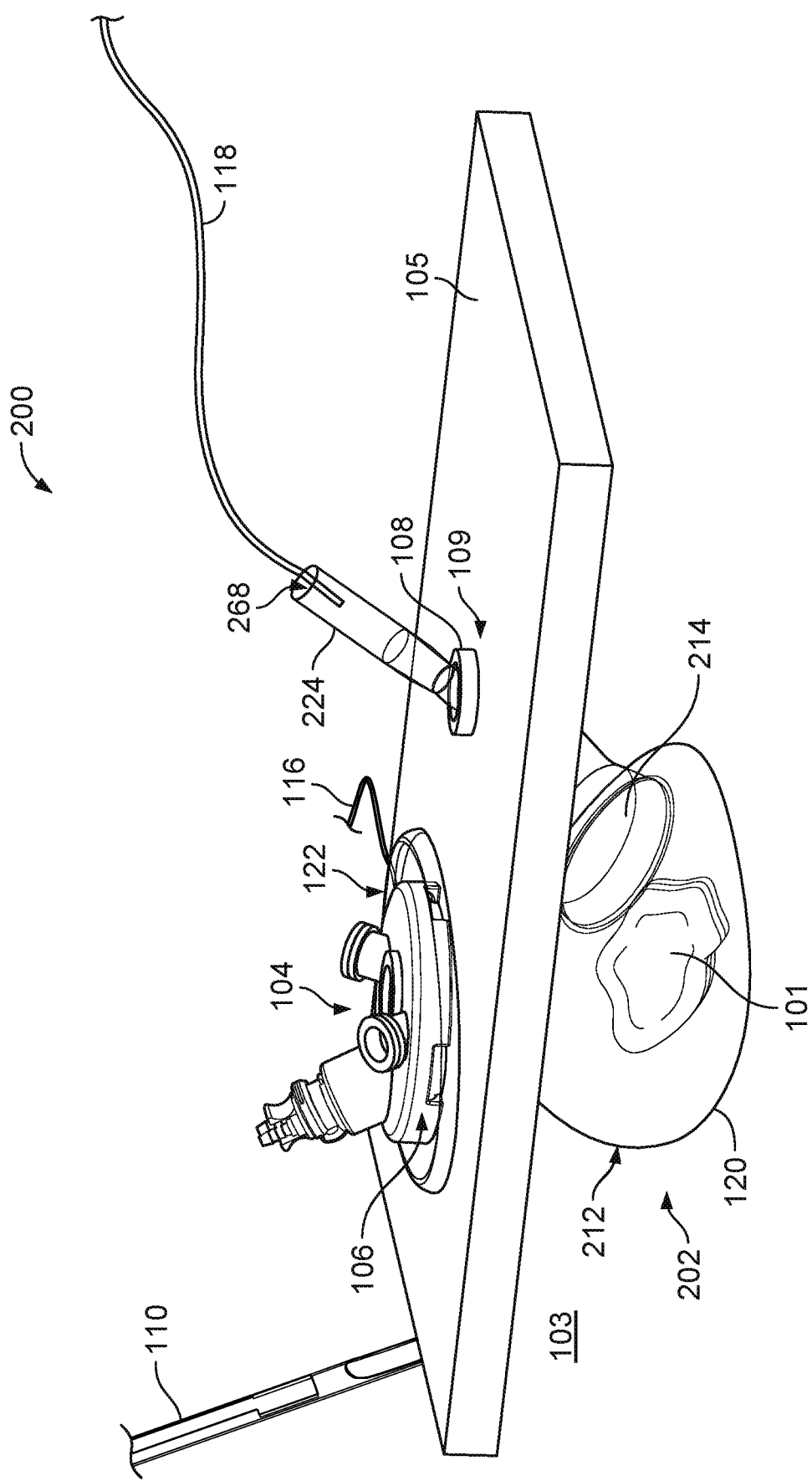
FIG. 15 is a perspective view of a tissue containment system interfaced with an abdomen of a patient.

While certain embodiments have been described above, other embodiments are possible. For example, while the tissue containment system 100 has been described and illustrated as including the viewing window 114 disposed along a tip of the closed-ended portion 124 of the containment bag 112, in some embodiments, a tissue containment system that is otherwise substantially similar in construction and function to the tissue containment system 100 includes a viewing window that is disposed along a main portion of a containment bag. Referring to FIG. 15, a tissue containment system 200 includes a specimen container 202 that can be placed within the abdominal cavity 103 and the access cap 104, the wound liner 106, and the bag introducer 110 of the tissue containment system 100. As with the tissue containment system 100, the various components of the tissue containment system 200 can be provided as a kit of separate components that can be interfaced with each other and with the patient at the time of performing the laparoscopic procedure.

The specimen container 202 is shaped similarly to the specimen container 102 and includes a containment bag 212 and a viewing window 214. The specimen container 202 also includes the retainer ring 108, the drawstring tether 116, and the pull tether 118 of the specimen container 102. The containment bag 212 defines the main portion 120 and the open-ended portion 122 of the containment bag 112 and a closed-ended portion 224 by which an interior region of the specimen container 202 can be viewed with a tissue visualization device. The main portion 120 and the open-ended portion 122 are in fluid communication with each other, but fluidly isolated from the closed-ended portion 224. The open-ended portion 122 provides a single opening 226 of the specimen container 202 that can be manipulated by the drawstring tether 116, as discussed above with respect to the specimen containment system 100. The retainer ring 108 surrounds the closed-ended portion 224 of the containment bag 212 and serves to fix a position of the closed-ended portion 224 within the wound 109 within the abdominal wall 105.

The closed-ended portion 224 is shaped similarly to the closed-ended portion 124 of the containment bag 112 and accordingly projects from the main portion 120 to facilitate positioning of the closed-ended portion 224 within the wound 109. A sealed interface between the closed-ended portion 224 and the main portion 120 defines a position of the viewing window 214 along the containment bag 212 such that contact between the viewing window 214 and a tissue visualization device provides a tactile indication of an orientation and a position of the containment bag 212 within the abdominal cavity 103. In this manner, the viewing window 214 further provides a closed end of the closed-ended portion 224 that is arranged to remain inside of the abdominal cavity 103 during morcellation of the tissue 101. The closed-ended portion 224 defines an opening 268 in a direction opposite the viewing window 214 to provide access to a tissue visualization device. The viewing window 214 is an optically clear, flexible wall that is sized and shaped to be contacted across its area by a distal end of a tissue visualization device for viewing the interior region of the specimen container 202. The viewing window 214 is stiffer and less compliant than the containment bag 212 and provides an unobstructed wall (e.g., without interior seam lines) that is impenetrable to engaging laparoscopic devices. The viewing window 214 provides the tissue containment system 200 with an access port (e.g., a vision access port) that is separate from the access cap 104 such that a region in which a tissue visualization device is placed is out of the way of a region that may contain other surgical tools.

The containment bag 212 has the same material formulation and construction of the containment bag 112 and is therefore compliant, impermeable, relatively puncture resistant, and translucent, as discussed above with respect to the containment bag 112. The closed-ended portion 224 of the containment bag 212 has the same size and the shape as those of the closed-ended portion 124 of the containment bag 112. Accordingly, the containment bag 212 provides a large, safe working zone in which the tissue 101 can be morcellated within the containment bag 212 at a location remote (e.g., spaced apart) from organs in the abdominal cavity 103, while being small enough to avoid significant infolding or double layering of the containment bag 212 within the abdominal cavity 103.

The viewing window 214 provides an optically clear barrier between the tissue visualization device and the containment bag 212. Accordingly, the viewing window 214 is the only portion of the tissue containment system 200 that may separate a distal end of the tissue visualization device from the interior region of the containment bag 212. The viewing window 214 is typically attached to the main portion 120 of the containment bag 212 via a heat seal, an ultrasonic weld, or glue. The viewing window 214 is typically made of one or more clear plastic materials, such as polycarbonate or other medical grade clear engineering resins. The viewing window 214 may have a round (e.g., circular) or non-round shape and typically has a total cross-sectional area of about 7 cm² to about 10 cm² (e.g., about 8 cm²).

The tissue containment system 200 can be used similarly to the tissue containment system 100 to contain a tissue during a laparoscopic procedure, as discussed above with respect to FIGS. 8-14, except that a tissue visualization device is inserted through the opening 268 of the closed-ended portion 224 to access the viewing window 214 instead of being inserted into a viewing window constructed like that of the viewing window 114.

In some embodiments, a tissue containment system that is otherwise substantially similar in construction and function to the tissue containment system 200 may include a containment bag that is closed off (e.g., fluidly isolated) from the closed-ended portion 224, except that the containment bag is optically clear (e.g., transparent) and does not include a separate viewing window (e.g., the viewing window 214). For example, such a containment bag can include an open-ended portion, a closed-ended portion, and a main portion that are similar in construction and function to the respective portions of the containment bag, 212, except that the bag is optically clear and the main portion does not include the opening defined by the viewing window 214. In other words, the wall (e.g., sheet material) of the main portion of the containment bag extends across an area to which the closed-ended portion is sealed (e.g., an interior end of the closed-ended portion), such that the containment bag is simply formed as an optically clear (e.g., transparent) bag that defines a single opening (e.g., like the opening 126) along one side and that includes a sleeve (e.g., like the closed-ended portion 224) extending therefrom along a second side. A tissue containment system including such a containment bag can be used similarly to the tissue containment system 200 to contain a tissue during a laparoscopic procedure.

Figure 16:
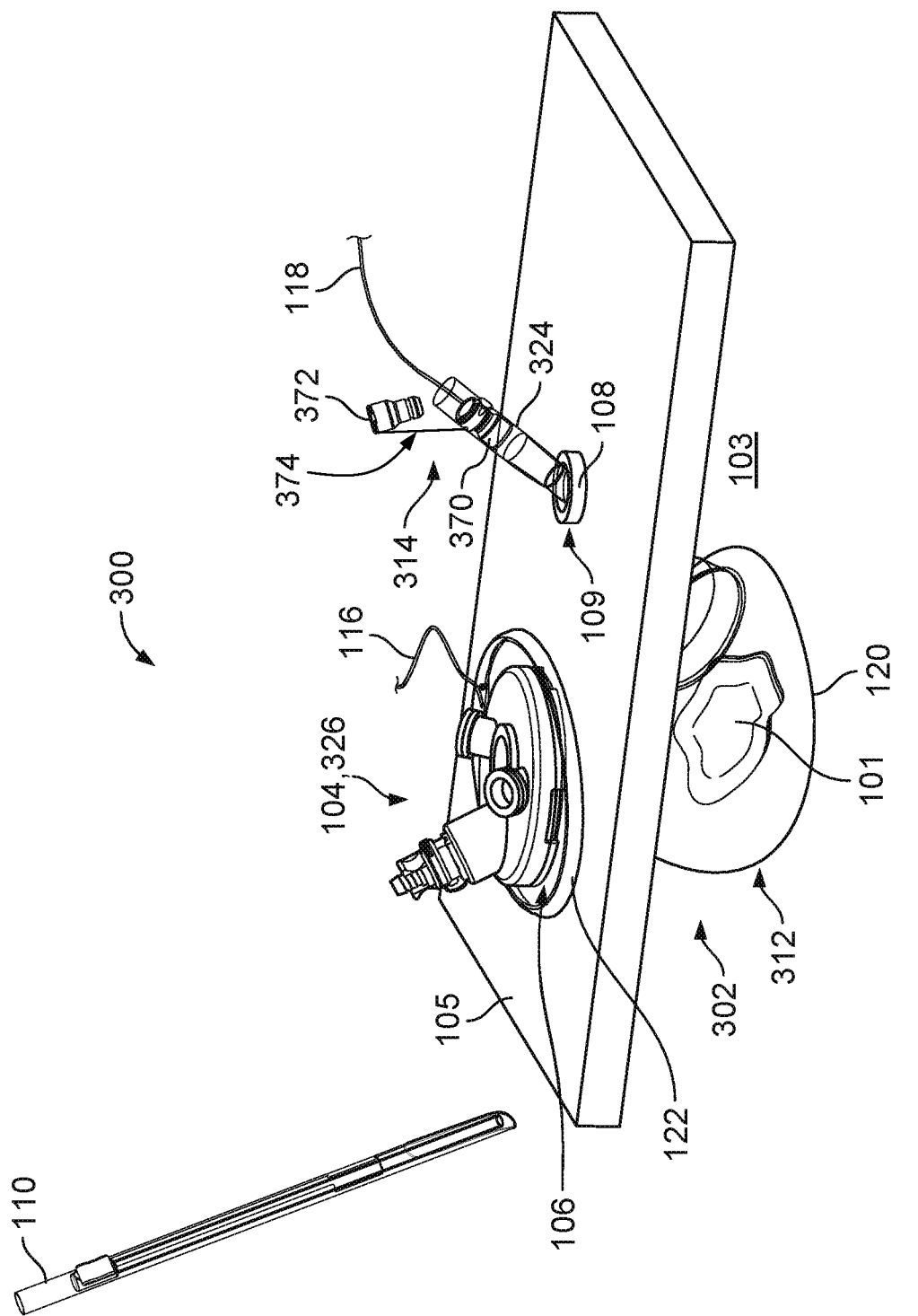
FIG. 16 is a perspective view of a tissue containment system interfaced with an abdomen of a patient, with a closeable end in an open configuration.
Figure 17:
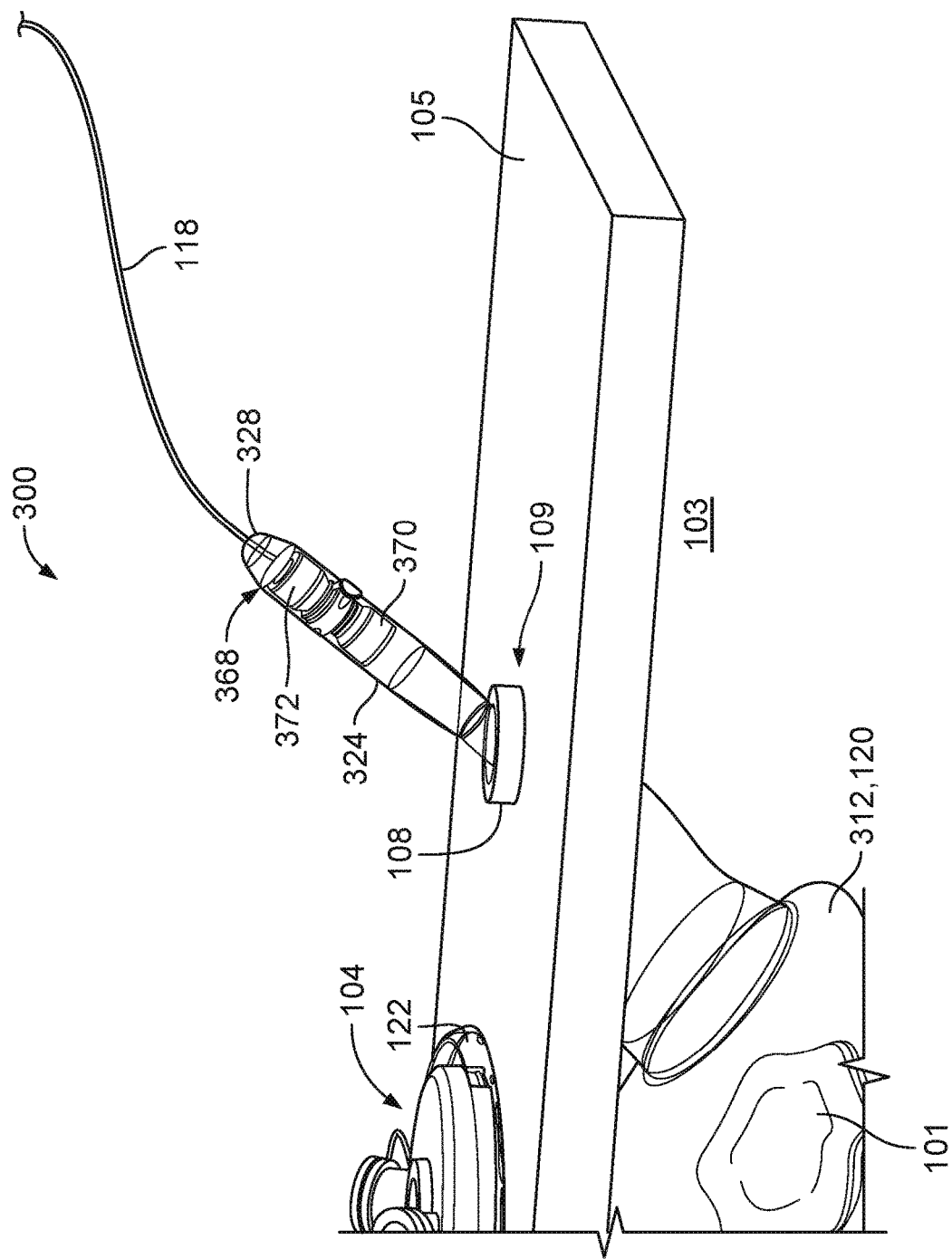
FIG. 17 is a perspective view of the closeable end of the tissue containment system of FIG. 16 in a closed configuration.

While the tissue containment systems 100, 200 have been described and illustrated as including the viewing windows 114, 214 that provide closed endoscopic access ports that isolate the tissue visualization device from the interior regions of the containment bags 112, 212, in some embodiments, a tissue containment system that is otherwise substantially similar in construction to either of the tissue containment systems 100, 200 includes an open endoscopic access port. For example, as shown in FIGS. 16 and 17, a tissue containment system 300 includes a specimen container 302 that can be placed within the abdominal cavity 103 and the access cap 104, the wound liner 106, and the bag introducer 110 of the tissue containment system 100. As with the tissue containment system 100, the various components of the tissue containment system 300 can be provided as a kit of separate components that can be interfaced with each other and with the patient at the time of performing the laparoscopic procedure.

The specimen container 302 is shaped similarly to the specimen container 102 and includes a containment bag 312 and a sealable connector 314 (e.g., a male/female connection mechanism, such as a quick non-spill disconnection). The specimen container 302 also includes the retainer ring 108, the drawstring tether 116, and the pull tether 118 of the specimen container 102. The containment bag 312 includes the main portion 120 and the open-ended portion 122 of the containment bag 112, and a closeable end portion 324 by which an interior region of the specimen container 302 can be viewed with a tissue visualization device. The main portion 120, the open-ended portion 122, and the closeable end portion 324 are in fluid communication with one another. The open-ended portion 122 provides an opening 326 of the specimen container 302 that can be manipulated by the drawstring tether 116, as discussed above with respect to the specimen containment system 100. The retainer ring 108 surrounds the closeable end portion 324 of the containment bag 312 and serves to fix a position of the closeable end portion 324 within the wound 109 within the abdominal wall 105.

The closeable end portion 324 is shaped similarly to the closed-ended portion 124 of the containment bag 112 and accordingly projects from the main portion 120 to facilitate positioning of the closeable end portion 324 within the wound 109. The closeable end portion 324 also defines a position of the sealable connector 314 along the containment bag 312 and a cutting plane 368 located just above (e.g., proximal to) the sealed connector 314 and defining a tip 328 of the closeable end portion 324. Because the closeable end portion 324 is sized and shaped to extend through the wound 109 outside of the patient, the closeable end portion 324 can accommodate an inverted placement of the sealed connector 314 within the retainer ring 108. The pull tether 118 is attached to the closeable end portion 324 and can be used to pull the closeable end portion 324 (e.g., including the retainer ring 108) through the wound 109 and out of the patient.

The sealable connector 314 includes a female connector 370 that is secured to a wall of the closeable end portion 324 and a complementary male connector 372 that is attached to the closeable end portion 324 by a tether 374. Once the tip 328 of the closeable end portion 324 is cut off, the male connector 372 is accessible and can be removed from the female connector 370. The female connector 370 is sized to allow passage of a distal end of a tissue visualization device for viewing the interior region of the specimen container 302. The sealable connector 314 provides the tissue containment system 300 with an access port (e.g., a vision access port) that is separate from the access cap 104 such that a region in which a tissue visualization device is placed is out of the way of a region that may contain other surgical tools. Following visualization of the interior region of the containment bag 312 with the tissue visualization device, the tissue visualization device can be removed from the female connector 370, and the male connector 372, still tethered to the containment bag 312, can be reattached to the female connector 370 to seal the containment bag 312.

The containment bag 312 has the same material formulation and construction of the containment bag 112 and is therefore compliant, impermeable, relatively puncture resistant, and translucent, as discussed above with respect to the containment bag 112. The closeable end portion 324 of the containment bag 312 generally has the same size and the same shape as those of the closed-ended portion 124 of the containment bag 112. Accordingly, the containment bag 312 provides a large, safe working zone in which the tissue 101 can be morcellated within the containment bag 312 at a location remote (e.g., spaced apart) from organs in the abdominal cavity 103, while being small enough to avoid significant infolding or double layering of the containment bag 312 within the abdominal cavity 103.

The sealable connector 314 is typically attached to the closeable end portion 324 of the containment bag 312 via a heat seal, an ultrasonic weld, or one or more mechanical means (e.g., an o-ring, a nut, etc.). The sealable connector 314 is typically made of one or more materials, such as polycarbonate or other materials. The female connector 370 may have an internal diameter of about 0.7 cm to about 1.0 cm (e.g., about 0.8 cm²) to allow passage of a tissue visualization device.

The tissue containment system 300 can be used similarly to the tissue containment system 100 to contain a tissue during a laparoscopic procedure, as discussed above with respect to FIGS. 8-14, except that the tip 328 of the closed-ended portion is cut off and the male connector 372 is removed to allow insertion of a tissue visualization device through the female connector 370 to view the interior region of the containment bag 312 directly instead of viewing the interior region through a viewing window constructed like that of the viewing windows 114, 214.

While the tissue containment systems 100, 200, 300 have been described and illustrated as being used with a tissue morcellator, in some implementations, the tissue containment systems 100, 200, 300 may be used with another type of tissue removal, reduction, and/or manipulation device, such as a scalpel, an electrosurgical scalpel, or a vacuum (e.g., suction) device.

While the containment bags 112, 212, 312 of the tissue containment systems 100, 200, 300 have been described as translucent, in some embodiments, a tissue containment system that is otherwise substantially similar in construction and function to any of the tissue containment systems 100, 200, 300 can include a containment bag that is optically clear (e.g., transparent) to further facilitate imaging of an interior region of the containment bag with a tissue visualization device.

While the tissue containment systems 100, 200, 300 have been described and illustrated as having certain sizes, defining certain volumes, and having certain shapes, in some embodiments, a tissue containment system that is otherwise substantially similar in construction and function to any of the tissue containment systems 100, 200, 300 can have different sizes, volumes, and/or shapes. In some examples, a tissue containment system can include a containment bag and/or other components that are sized particularly for child patients (e.g., a pediatric tissue containment system), adult patients, patients within a particular age range, or patients with particular medical conditions.

Additionally, other embodiments and implementations are within the scope of the following claims.

What is claimed is:

1. A tissue containment system, comprising:
   a bag body configured to be placed in an abdominal cavity of a patient and defining an interior region configured to contain a loose tissue specimen, the bag body further defining:
      a main portion sized to accommodate the loose tissue specimen,
      an open-ended portion defining an opening sized to receive the loose tissue specimen and arranged to extend from the main portion outside of the patient while the main portion is disposed in the abdominal cavity, and
      an invertible portion arranged to extend from the main portion outside of the patient while the main portion is disposed within the abdominal cavity, the invertible portion being invertible to form a double wall layer that is sized to accommodate a tissue visualization device;
   a rigid viewing window sealed to an end of the invertible portion that is opposite to the main portion such that the rigid viewing window is positionable outside of the patient while the main portion is disposed within the abdominal cavity, the rigid viewing window being at least partially transparent and being configured to receive the tissue visualization device for viewing the interior region of the bag body when the invertible portion is inverted to form the double wall layer around the tissue visualization device within the patient; and
   an access cap configured to close the opening of the open-ended portion of the bag body and comprising:
      an entry port configured to allow passage of a tissue removal device into the interior region of the bag body, and
      an insufflation port spaced apart from the entry port and configured to deliver fluid to the interior region of the bag body.

2. The tissue containment system of claim 1, wherein the main portion and the invertible portion are in fluid communication with each other.

3. The tissue containment system of claim 1, further comprising a retainer attached to an external surface of the invertible portion.

4. The tissue containment system of claim 3, wherein the retainer is adjustable from a first extent that is smaller than a wound within a wall of the abdominal cavity for passage through the wound to a second extent that is larger than the wound for retaining the invertible portion outside of the patient.

5. The tissue containment system of claim 1, wherein a wall of the bag body is configured to thermally isolate the interior region of the bag body from the abdominal cavity.

6. The tissue containment system of claim 1, wherein the invertible portion of the bag body and the viewing window together isolate the tissue visualization device from the loose tissue specimen and from the abdominal cavity.

7. The tissue containment system of claim 1, further comprising a wound liner that is configured to surround the open-ended portion of the bag body.

8. The tissue containment system of claim 7, wherein the access cap is configured to be secured to the wound liner in an airtight manner.

9. The tissue containment system of claim 1, further comprising an elongate bag introducer configured to introduce the bag body into the abdominal cavity.

10. The tissue containment system of claim 9, wherein the entry port for the tissue removal device is sized to provide a passageway for the elongate bag introducer.

11. The tissue containment system of claim 1, wherein the tissue removal device comprises a morcellator.

12. The tissue containment system of claim 1, wherein the tissue visualization device comprises an endoscope.

13. The tissue containment system of claim 1, wherein the access cap further comprises:
   a first working port spaced apart from the entry port and from the insufflation port and sized to allow passage of a first surgical instrument into the interior region of the bag body, and
   a second working port sized to allow passage of a second surgical instrument into the interior region of the bag body,
   wherein the first and second working ports are disposed along opposite sides of the entry port.

14. The tissue containment system of claim 1, wherein the rigid viewing window is made of an optically clear material.

15. The tissue containment system of claim 1, wherein the rigid viewing window forms a U-shaped receptacle for receiving the tissue visualization device.

16. The tissue containment system of claim 1, wherein the open-ended portion and the invertible portion extend from the main portion in substantially opposite directions.

17. A method of containing a loose tissue specimen within an abdominal cavity of a patient, the method comprising:
   introducing a containment bag into the abdominal cavity;

moving a loose tissue specimen within the abdominal cavity into a main portion of the containment bag through an opening of an open-ended portion of the containment bag;

positioning the open-ended portion of the containment bag outside of the patient while the main portion is disposed within the abdominal cavity;

positioning an invertible portion of the containment bag outside of the patient while the main portion is disposed within the abdominal cavity;

securing an access cap to the open-ended portion of the containment bag outside of the patient to close the opening;

placing a tissue visualization device against a rigid viewing window sealed to an end of the invertible portion disposed outside of the patient;

advancing the tissue visualization device against the rigid viewing window into the invertible portion to cause the invertible portion to form a double wall layer around the tissue visualization device within the patient, viewing an interior region of the containment bag with the tissue visualization device through the rigid viewing window;

delivering a fluid to the interior region of the containment bag through an insufflation port of the access cap to insufflate the containment bag; and passing a tissue removal device into the interior region of the containment bag through an entry port of the access cap, the entry port being spaced apart from the insufflation port.

* * * * *